(12) United States Patent
Holmes et al.

(10) Patent No.: US 6,949,291 B2
(45) Date of Patent: Sep. 27, 2005

(54) TWISTED POLYMERS, USES THEREOF AND PROCESSES FOR THE PREPARATION OF STATISTICAL COPOLYMERS

(75) Inventors: Andrew Holmes, Cambridge (GB); Rainer Martin, Basel (CH); Ian Rees, Cambridge (GB); Cedric Fischmeister, Rennes (FR); Yuguang Ma, Changchun (CN); Franco Cacialli, Cambridge (GB)

(73) Assignee: Cambridge Display Technology Limited, Cambridgeshire (GB)

( * ) Notice: Subject to any disclaimer, the term of this patent is extended or adjusted under 35 U.S.C. 154(b) by 0 days.

(21) Appl. No.: 10/381,583

(22) PCT Filed: Sep. 26, 2001

(86) PCT No.: PCT/GB01/04303

§ 371 (c)(1),
(2), (4) Date: Jun. 23, 2003

(87) PCT Pub. No.: WO02/26856

PCT Pub. Date: Apr. 4, 2002

(65) Prior Publication Data

US 2004/0097699 A1 May 20, 2004

Related U.S. Application Data

(60) Provisional application No. 60/253,876, filed on Nov. 29, 2000.

(30) Foreign Application Priority Data

Sep. 26, 2000 (GB) .............................................. 0023538
Apr. 6, 2001 (GB) .............................................. 0108761

(51) Int. Cl.[7] .......................... B32B 27/00; C08G 83/00
(52) U.S. Cl. .................... 428/411.1; 528/245; 528/247; 528/265; 528/377; 528/380; 528/417; 528/423
(58) Field of Search ...................... 428/411.1; 528/245, 528/247, 265, 377, 380, 417, 423

(56) References Cited

U.S. PATENT DOCUMENTS 5,512,654 A  4/1996  Holmes et al. .............. 528/373

(Continued)

FOREIGN PATENT DOCUMENTS

EP  0 707 020  8/2000

(Continued)

OTHER PUBLICATIONS

Shibaev et al., Polymer Science—Series A, vol. 40, No. 11, pp. 1049–1053, Nov. 1998.*

(Continued)

*Primary Examiner*—Ramsey Zacharia
(74) *Attorney, Agent, or Firm*—Marshall, Gerstein & Borun LLP

(57) ABSTRACT

The invention relates to optical devices comprising a substrate and at least one semiconductive polymer supported by said substrate, wherein said semiconductive polymer is a copolymer in which one of the repeat units is a group of formula (I) or a homopolymer in which the repeat unit is a group of formula (I):

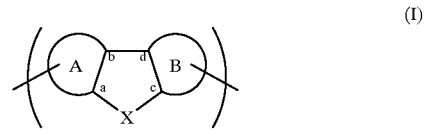

wherein:

A and B are the same or different and each comprises wholly or partially an aryl moiety or a heteroaryl moiety, said moiety in A being fused to the bond a-b and said moiety in B being fused to the bond c-d, and X is a linking unit, X being such that there is a torsion angle of at least 5° between the bond a-b and the bond c-d about the bond b-d.

The invention also relates to semiconductive polymers, monomers for preparing same, and methods for preparing random statistical conjugated polymers.

23 Claims, 8 Drawing Sheets

U.S. PATENT DOCUMENTS

| | | | |
|---|---|---|---|
| 5,514,878 A | 5/1996 | Holmes et al. | 257/40 |
| 5,672,678 A | 9/1997 | Holmes et al. | 528/373 |
| 5,708,130 A | 1/1998 | Woo et al. | 528/397 |
| 5,777,070 A | 7/1998 | Inbasekaran et al. | 528/394 |
| 5,962,631 A | 10/1999 | Woo et al. | 528/397 |

FOREIGN PATENT DOCUMENTS

| | | |
|---|---|---|
| WO | WO 90/13148 | 11/1990 |
| WO | WO 93/14177 | 7/1993 |
| WO | WO 94/29883 | 12/1994 |
| WO | WO 95/06400 | 3/1995 |
| WO | WO 99/48160 | 9/1999 |
| WO | WO 99/54385 | 10/1999 |
| WO | WO 99/54943 | 10/1999 |
| WO | WO 00/22026 | 4/2000 |
| WO | WO 00/53656 | 9/2000 |
| WO | WO 00/55927 | 9/2000 |
| WO | WO 01/07052 | 2/2001 |
| WO | WO 01/42331 A1 | 6/2001 |

OTHER PUBLICATIONS

Bernius et al., "Progress with Light–Emitting Polymers," *Adv. mater.*, 12(23):1737–1750 (Dec. 1, 2000).

Bharathan et al., "Polymer electroluminescent devices processed by inkjet printing: I. Polymer light–emitting logo," *Appl. Phys. Lett.*, 72(21):2660–2662 (1998).

Bliznyuk et al., "Electrical and Photoinduced Degradation of Polyfluorene Based Films and Light–Emitting Devices," *Macromolecules*, 32:361–369 (1999).

Burroughes et al, "Light–emitting diodes based on conjugated polymers," *Nature*, 347:539–541 (1990).

Chang et al., "Dual–color polymer light–emitting pixels processed by hybrid inkjet printing," *Appl. Phys. Lett.*, 73(18):2561–2563 (1998).

Cho et al., "Statistical Copolymers for Blue–Light–Emitting Diodes," *Macromolecules;* 32:1476–1481 (1999).

Grice et al., "High brightness and efficiency blue light–emitting polymer diodes," *Appl. Phys. Lett.*, 73(5):629–631 (1998).

Hall et al., "The Relation between Configuration and Conjugation in Diphenyl Derivatives. Part IX. Some Tetrachloro–2:2'–bridged Compounds," *J. Chem. Soc.*, 4584–4591 (1957).

Hebner et al., "Ink–jet printing of doped polymers for organic light emitting devices," *Appl. Phys. Lett.*, 72(5):519–521 (1998).

Hong et al., "Origin of the Broken Conjugation in *m*–Phenylene Linked Conjugated Polymers," *Macromolecules*, 34: 6474–6481 (Aug. 1, 2001).

Kim et al., "Improved operational stability of polyfluorene–based organic light–emitting diodes with plasma–treated indium–tin–oxide anodes," *App. Phys. Lett.*, 74(21):3084–3086 (1999).

Klaerner et al., "Dendrimers as End Groups in Rigid Rod Polymers based on Di–*n*–hexylfluorene–2,7–diyl; Polymeric Molecular Dumbells," *American Chemical Society*, 216:300–POLY, Part 3 (Abstract of Papers), pp. 1006–1007 (1998).

Kraft et al., "Electroluminescent Conjugated Polymers—Seeing Polymers in a New Light," *Angew. Chem. Int. Ed.*, 37:403–428 (1998).

Littke et al., "A Versatile Catalyst for Heck Reactions of Aryl Chlorides and Aryl Bromides under Mild Conditions," *J. Am. Chem. Soc.*, 123:6989–7000 (Jun. 28, 2001).

Miteva et al., "Improving the Performance of Polyfluorene–Based Organic Light–Emitting Diodes via End–capping," *Adv. Mater.*, 13(8):565–570 (Apr. 18, 2001).

Miyaura et al., "Palladium–Catalyzed Cross–Coupling Reaction of Phenylboronic Acid with Haloarenes in the Presence of Bases," *Synth. Commun.*, 11(7):513–519 (1981).

Pei et al., "Efficient Photoluminescence and Electroluminescence from a Soluble Polyfluorene," *J. Am. Chem. Soc.*, 118:7416–7417 (1996).

Scherf et al., "The Synthesis of Ladder Polymers," *Adv. Polym. Sci.*, 123:1–40 (1995).

Service, "Self–Assembled LEDs Shine Brightly," *Science*, 279:1135 (1998).

Setayesh et al., "Bridging the Gap between Polyfluorene and Ladder–Poly–*p*–phenylene: Synthesis and Characterization of Poly–2,8–indenofluorene," *Macromolecules*, 33:2016–2020 (Mar. 3, 2000).

Setayesh et al., "Polyfluorenes with Polyphenylene Dendron Side Chains: Toward Non–Aggregating, Light–Emitting Polymers," *J. Am. Chem. Soc.*, 123:946–953 (Jan. 16, 2001).

Sheats et al., "Organic Electroluminescent Devices," *Science*, 273:884–888 (1996).

Yamamoto, "Electrically Conducting And Thermally Stable π–Conjugated Poly (Arylene)s Prepared By Organometallic Processes," *Prog. Polym. Sci.*, 17:1153–1205 (1992).

CAS Registry No. 63918–66–1.

Ōki et al., "Effects of para–Substituents on the Rates of Inversion of Biphenyl Derivatives. I. 5,7–Dihydrodibenzo [*c,e*]thiepins," *Bull. Chem. Society of Japan*, 44:262–265 (1971).

Truce et al., "Preparation and geometry of o,o'–bridged biphenyls containing sulfur or selenium in the bridge," *Chemical Abstracts* 51:2817c (1957).

Great Britain Search Report in GB 0108761.8 dated Nov. 7, 2001.

International Search Report in PCT/GB01/04303 dated Nov. 26, 2001.

Written Opinion for PCT/GB01/04303 (undated).

Written Opinion for PCT/GB01/04303 dated Jul. 22, 2002.

International Preliminary Examination Report in PCT/GB01/04303 dated Jan. 15, 2003.

* cited by examiner

Film PL of Octylamine functionalised Twisted Copolymers

N-50 a:b=0.5:0.5
N-40 a:b=0.4:0.6
N-30 a:b=0.3:0.7
N-20 a:b=0.2:0.8
N-10 a:b=0.1:0.9

Film PL of Sulfone Functionalised Twisted Copolymers

SO2-50 a:b=0.5:0.5
SO2-40 a:b=0.4:0.6
SO2-30 a:b=0.3:0.7
SO2-20 a:b=0.2:0.8
SO2-10 a:b=0.1:0.9

Film PL of Ether functionalised Twisted Copolymers

O-50 a:b=0.5:0.5
O-40 a:b=0.4:0.6
O-30-30 a:b=0.3:0.7
O-20-20 a:b=0.2:0.8
O-10-10 a:b=0.1:0.9

S-50 a:b=0.5:0.5
S-40 a:b=0.4:0.6
S-30-30 a:b=0.3:0.7
S-20-20 a:b=0.2:0.8
S-10-10 a:b=0.1:0.9

S-25  a:b= 0.25:0.75

TWISTED POLYMERS, USES THEREOF AND PROCESSES FOR THE PREPARATION OF STATISTICAL COPOLYMERS

CROSS-REFERENCE TO RELATED APPLICATIONS

This is the U.S. national phase of International Application No. PCT/GB01/04303, filed Sep. 26, 2001, which claims the benefit under 35 U.S.C. § 119(e) of U.S. Provisional Application Ser. No. 60/253,876, filed Nov. 29, 2000, the full disclosures of which, in their entirety, are hereby incorporated by reference.

BACKGROUND OF THE INVENTION

1. Field of the Invention

The present invention relates to optical devices which comprise a substrate which supports at least one semiconductive polymer which is less prone to aggregation than conventional poly(fluorene)-based polymers and which exhibits a blue-shifted emission. It also relates to novel homopolymers and copolymers for use in said devices, monomers for the preparation of said polymers and a process for the preparation of statistical copolymers which is particularly suitable for the preparation of the polymers of the present invention.

2. Description of Related Technology

In recent years, there has been considerable interest in conjugated polymers. These are polymers which possess a delocalised pi-electron system along the polymer backbone. The delocalised pi-electron system confers semiconducting properties to the polymer and gives it the ability to support positive and negative charge carriers with high mobilities along the polymer chain. Thin films of these conjugated polymers can be used in the preparation of optical devices such as light-emitting devices. These devices have numerous advantages over devices prepared using conventional semiconducting materials, including the possibility of wide area displays, low dc working voltages and simplicity of manufacture. Devices of this type are described in, for example, WO-A-90/13148, U.S. Pat. No. 5,512,654 and WO-A-95/06400.

The world market for displays based on organic and polymeric light-emitting materials has recently been estimated by Stanford Resources, Inc., to be $200 million in the year 2002 with a strong growth rate which fuels the high industrial interest in this area (D. E. Mentley, "Flat Information Displays: Market and Technology Trends", 9[th] edition, 1998). Efficient and highly stable LED devices with low power consumption, which fulfill commercial requirements, have been prepared by a number of companies and academic research groups (see, for example, A. C. Grimsdale et al., *Angew. Chem. Int. Ed.* 1998, 37, 402; R. H. Friend et al., *Nature* 1999, 397, 12). As a result of this very fast development of polymer-based LEDs (PLEDs) compared to the development of inorganic LEDs (Sheats et al., *Science* 1996, 273, 884) the first effective monochromatic active- and passive-addressed matrix displays have been demonstrated to work and in 1999 PHILIPS announced the initiation of a manufacturing line for PLED display components (e.g. LEP backlights for the automotive and telecommunications industries).

At the moment, great efforts are dedicated to the realization of a full-colour, all plastic screen. The major challenges to achieve this goal are: (1) access to conjugated polymers emitting light of the three basic colours red, green and blue; and (2) the conjugated polymers must be easy to process and fabricate into full-colour display structures. PLED devices show great promise in meeting the first requirement, since manipulation of the emission colour can be achieved by changing the chemical structure of the conjugated polymers. However, while modulation of the chemical nature of conjugated polymers is often easy and inexpensive on the lab scale it can be an expensive and complicated process on the industrial scale. The second requirement of the easy processability and build-up of full-colour matrix devices raises the question of how to micro-pattern fine multicolour pixels and how to achieve full-colour emission. Inkjet printing and hybrid inkjet printing technology have recently attracted much interest for the patterning of PLED devices (see, for example, R. F. Service, *Science* 1998, 279, 1135; Wudl et al., *Appl. Phys. Lett.* 1998, 73, 2561; J. Bharathan, Y. Yang, *Appl. Phys. Lett.* 1998, 72, 2660; and T. R. Hebner, C. C. Wu, D. Marcy, M. L. Lu, J. Sturm, *Appl. Phys. Lett.* 1998, 72, 519).

In order to contribute to the development of a full-colour display, conjugated polymers exhibiting direct colour-tuning, good processability and the potential for inexpensive large-scale fabrication are sought. The step-ladder polymer poly-2,7-fluorene has been the subject of much research into blue-light emitting polymers (see, for example, A. W. Grice, D. D. C. Bradley, M. T. Bernius, M. Inbasekaran, W. W. Wu, and E. P. Woo, *Appl. Phys. Lett.* 1998, 73, 629; J. S. Kim, R. H. Friend, and F. Cacialli, *Appl. Phys. Lett.* 1999, 74, 3084; WO-A-00/55927 and M. Bernius et al., *Adv. Mater.*, 2000, 12, No. 23, 1737). This class of conjugated polymers possesses excellent processability, endowed by the attachment of solubilizing groups at the remote C-9 position, without hampering the extended conjugation and therefore leading to high fluorescence quantum yields in the solid state (up to 79%) (see, for example, Q. Pei, Y. Yang, *J. Am. Chem. Soc.* 1996, 118, 7416). Other benefits of poly-2,7-fluorene are its excellent thermal ($T_d$>400° C.) and chemical stability and its good film forming properties. The rigid nature of this polymer, however, enhances inter-chain aggregation leading to an undesired red-shift of the emission colour and a decreasing luminescence efficiency through excimer formation (see, for example, V. N. Bliznyuk, S. A. Carter, J. C. Scott, G. Klarner, R. D. Miller, and D. C. Miller, *Macromolecules*, 1999, 32, 361). Aggregation has been decreased to some extent through statistical copolymerization of 2,7-dibromofluorene with other halogenated monomers.

The process to make homo- and copolymers based on 9,9-disubstituted fluorene monomers depends on the metal-mediated cross coupling of both AA-BB and AB type monomers. There is now a considerable prior art in the field. Such copolymers may be made by the cross coupling of dibromo-substituted monomers by contacting them with a Ni(0) catalyst formed in situ from a Ni(II) salt (the Yamamoto coupling, *Progress in Polymer Science*, Vol. 17, p.1153, 1992) (E. P. Woo et al., U.S. Pat. Nos. 5,708,130; 5,962,631). A Pd(0) mediated cross coupling between arylboronic acids and esters and aryl or vinyl halides (the Suzuki coupling, A. Suzuki et al., *Synth. Commun.*, 1981, 11, 513) has been developed in the presence of a phase transfer catalyst and an inorganic base to make relatively high quality poly(fluorene) derivatives for applications as PLEDs (M. Inbasekaran, U.S. Pat. No. 5,777,070). Extension to various comonomers having hole transporting properties has also been realised (WO-A-99/54385). In a further development a combination of a catalyst and a base was selected to convert the boron functional groups into —$BX_3^-$ where X is either F or OH (WO-A-00/53656).

As noted above, it is well known that a major disadvantage of poly(fluorene)-based homopolymers is their tendency to aggregate in the solid state, resulting in the formation of excited state complexes (excimers) under conditions of fluorescence through stimulation by photoexcitation or double charge injection (electroluminescence). One way of reducing this tendency is to employ copolymers to break up aggregation (see U.S. Pat. No. 5,777,070; D. Kim, et al., *Macromolecules*, 1999, 32, 1476). Another approach is to use ladder-like planarised polymers (U. Scherf and K. Müllen, *Adv. Polym. Sci.*, 1995, 123, 1) and poly(indenofluorenes (S. Setayesh et al., *Macromolecules*, 2000, 33, 2016). Dendrimer substituents as end caps (G. Klaerner, R. D. Miller and C. J. Hawker, Abstracts of Papers of the American Chemical Society, 216: 300-POLY, Part 3 Aug. 23 1998) and at the 9-position of the fluorene building block (S. Setayesh et al., *J. Am. Chem. Soc.*, 2001, 123, 946) have been used to inhibit aggregation. Hole trapping end groups also enhance device performance, possibly through inhibition of aggregate formation.(T. Miteva et al., *Adv. Mater.*, 2001, 13, 565). It has been noted that poly(1,4-phenylene vinylene) homo- and copolymers carrying a 2,3-disubstitution pattern show a tendency to twist, and this distortion has been used to improve luminescence efficiency of polymer derivatives (see WO-A-01/07052). The origin of the broken conjugation in the backbone m-linked polyphenylenes has recently been discussed by S. Y. Hong et al., *Macromolecules*, 2001, 34, 6474.

It is highly desirable to develop electroluminescent polymers which reduce the aggregation seen in poly(fluorene)-based polymers. In this invention the design of electroluminescent polymers incorporating comonomers based on homologues of fluorene derivatives and optical devices incorporating said polymers is described.

GENERAL DESCRIPTION

Thus, in a first aspect of the present invention there is provided an optical device which comprises a substrate and at least one semiconductive polymer supported by said substrate, wherein said semiconductive polymer is a copolymer in which one of the repeat units is a group of formula (I) below or a homopolymer in which the repeat unit is a group of formula (I) below:

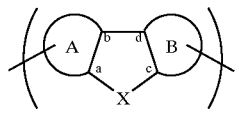

(I)

wherein:

A and B are the same or different and each comprises wholly or partially an aryl moiety or a heteroaryl moiety, said moiety in A being fused to the bond a-b and said moiety in B being fused to the bond c-d; and X is a linking unit, X being such that there is a torsion angle of at least 5° between the bond a-b and the bond c-d about the bond b-d.

The linking unit X is chosen such that A and B are twisted about the bond b-d so that the bonds a-b and c-d are not co-planar but instead there is a torsion angle of at least 5° between the bond a-b and the bond c-d about the bond b-d. Preferably, the torsion angle is from 5° to 75°; more preferably, the torsion angle is from 10° to 70°; yet more preferably, the torsion angle is from 30° to 60°; and most preferably, the torsion angle is from 40° to 55°.

The incorporation of the repeat units of formula (I) above results in the introduction of a degree of twisting to the polymer backbone. This has two effects. First, the overall extent of conjugation in the polymer is reduced which has the effect of increasing the HOMO-LUMO bandgap of these materials leading to a blue-shifted emission. Second, the introduction of twisting in the polymer backbone causes a reduction in the aggregation experienced in existing poly (fluorene)-based polymers.

In the group of formula (I) above, the aryl moiety may be, for example, an aromatic hydrocarbon moeity having from 6 to 14 carbon atoms in one or more rings which may optionally be substituted with at least one substituent, e.g. one or more substituents selected from the group consisting of nitro groups, cyano groups, amino groups, alkyl groups as defined below, haloalkyl groups as defined below, alkoxyalkyl groups as defined below, aryloxy groups as defined below and alkoxy groups as defined below. Examples of the aryl moieties include phenyl, naphthyl, phenanthryl and anthracenyl groups.

In the group of formula (I) above, the heteroaryl moiety may be, for example, a 5- to 7-membered aromatic heterocyclic moiety containing from 1 to 3 heteroatoms selected from the group consisting of sulfur atoms, oxygen atoms and nitrogen atoms, said moiety optionally being substituted with at least one substituent, e.g. one or more substituents selected from the group consisting of nitro groups, cyano groups, amino groups, alkyl groups as defined below, haloalkyl groups as defined below, alkoxyalkyl groups as defined below, aryloxy groups as defined below and alkoxy groups as defined below. Examples of such heteroaryl groups include furyl, thienyl, pyrrolyl, pyrazolyl, imidazolyl, oxazolyl, isoxazolyl, thiazolyl, isothiazolyl, triazolyl, tetrazolyl, thiadiazolyl, pyridyl, pyridazinyl, pyrimidinyl and pyrazinyl groups.

The alkyl groups above are straight or branched-chain alkyl groups having from 1 to 20 carbon atoms.

The haloalkyl groups above are alkyl groups as defined above which are substituted with at least one halogen atom.

The alkoxy groups above are straight or branched-chain alkoxy groups having from 1 to 20 carbon atoms.

The alkoxyalkyl groups above are alkyl groups as defined above which are substituted with at least one alkoxy group as defined above.

The aryl moiety of the aryloxy groups above is an aromatic hydrocarbon group having from 6 to 14 carbon atoms in one or more rings which may optionally be substituted with at least one substituent selected from the group consisting of nitro groups, cyano groups, amino groups, alkyl groups as defined above, haloalkyl groups as defined above, alkoxyalkyl groups as defined above and alkoxy groups as defined above.

Preferably, there is provided an optical device which comprises a substrate and at least one semiconductive polymer supported by said substrate, wherein said semiconductive polymer is a copolymer in which one of the repeat units is a group of formula (II) below or a homopolymer in which the repeat unit is a group of formula (II) below:

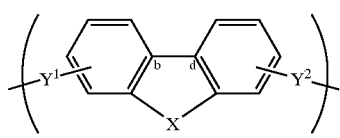

(II)

wherein:

$Y^1$ and $Y^2$ are the same or different and each represents a single bond or a linking unit that is conjugated with the phenyl group to which it is attached; and X is a linking unit, X being such that there is a torsion angle of at least 5° between the two phenyl groups about the bond b-d.

Where $Y^1$ or $Y^2$ is a linking unit that is conjugated with the phenyl group to which it is attached, the linking unit and the phenyl group to which it is attached together form a conjugated moiety which links the unit of formula (II) to the next unit in the copolymer or homopolymer. Thus, for example, $Y^1$ can be a phenyl group which is fused with the phenyl group to which it is attached to give a naphthylene linking unit, or an indenyl group which is fused with the phenyl group to which it is attached to give a fluorenyl linking unit.

More preferably, there is provided an optical device which comprises a substrate and at least one semiconductive polymer supported by said substrate, wherein said semiconductive polymer is a copolymer in which one of the repeat units is a group of formula (III) below or a homopolymer in which the repeat unit is a group of formula (III) below:

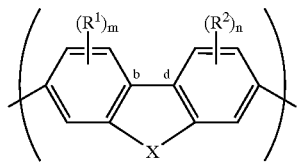

(III)

wherein:

m and n are the same or different and each is 0 or an integer of 1, 2 or 3;

$R^1$ and $R^2$ are same or different and each is selected from the group consisting of alkyl groups as defined above, haloalkyl groups as defined above, alkoxy groups as defined above, alkoxyalkyl groups as defined above, aryl groups (comprising aromatic hydrocarbon groups having from 6 to 14 carbon atoms in one or more rings which may optionally be substituted with at least one substituent selected from the group consisting of nitro groups, cyano groups, amino groups, alkyl groups as defined above, haloalkyl groups as defined above, alkoxyalkyl groups as defined above and alkoxy groups as defined above), aryloxy groups as defined above, and aryl groups comprising an alkyl group as defined above which is substituted with at least one aryl group as defined above; and X is a linking unit, X being such that there is a torsion angle of at least 5° between the two phenyl rings about the bond b-d. Where there is more than one group $R^1$ and/or $R^2$, then each $R^1$ or $R^2$ may be the same or different from the others.

In the optical devices of the present invention where the repeat unit in the copolymer or homopolymer is a group of formula (III), X is preferably a moiety of formula -A-B-C- wherein A, B and C are the same or different and each is selected from the group consisting of O, S, SO, $SO_2$, $NR^3$, $N^+(R^{3'})(R^{3''})$, $C(R^4)(R^5)$, $Si(R^{4'})(R^{5'})$, and $P(O)(OR^6)$, wherein:

$R^3$, $R^{3'}$ and $R^{3''}$ are the same or different and each is selected from the group consisting of hydrogen atoms, alkyl groups as defined above, haloalkyl groups as defined above, alkoxy groups as defined above, alkoxyalkyl groups as defined above, aryl groups as defined above, aryloxy groups as defined above, aralkyl groups as defined above, and alkyl groups as defined above which are substituted with at least one group of formula $—N^+(R^7)_3$ wherein each group $R^7$ is the same or different and is selected from the group consisting of hydrogen atoms, alkyl groups as defined above and aryl groups as defined above;

$R^4$, $R^5$, $R^{4'}$ and $R^{5'}$ are the same or different and each is selected from the group consisting of hydrogen atoms, alkyl groups as defined above, haloalkyl groups as defined above, alkoxy groups as defined above, halogen atoms, nitro groups, cyano groups, alkoxyalkyl groups as defined above, aryl groups as defined above, aryloxy groups as defined above, aralkyl groups as defined above and alkyl groups as defined above which are substituted with a substituent selected from the group consisting of aryl groups as defined above, heteroaryl groups as defined below, fluorenyl groups and spirobifluorenyl groups, said aryl, heteroaryl, fluorenyl and spirobifluorenyl groups being substituted with a disubstituted amino group the substituents of which are the same or different and are selected from the group consisting of aryl groups as defined above, heteroaryl groups as defined below, fluorenyl groups and spirobifluorenyl groups, or $R^4$ and $R^5$ together with the carbon atom to which they are attached represent a carbonyl group; and $R^6$ is selected from the group consisting of hydrogen atoms, alkyl groups as defined above, haloalkyl groups as defined above, alkoxyalkyl groups as defined above, aryl groups as defined above, aryloxy groups as defined above and aralkyl groups as defined above;

said heteroaryl groups are 5- to 7-membered aromatic heterocyclic groups containing from 1 to 3 heteroatoms selected from the group consisting of sulfur atoms, oxygen atoms and nitrogen atoms, said groups optionally being substituted with at least one substituent selected from the group consisting of nitro groups, cyano groups, amino groups, alkyl groups as defined above, haloalkyl groups as defined above, alkoxyalkyl groups as defined above, aryloxy groups as defined above and alkoxy groups as defined above.

Preferably, $R^3$, $R^{3'}$ and $R^{3''}$ are the same or different and each is selected from the group consisting of hydrogen atoms and alkyl groups having from 1 to 6 carbon atoms which are optionally substituted with a group of formula $—N^+(R^7)_3$ wherein each group $R^7$ is the same or different and is selected from the group consisting of hydrogen atoms and alkyl groups having from 1 to 6 carbon atoms; more preferably, $R^3$, $R^{3'}$ and $R^{3''}$ are the same or different and each represents an alkyl group having from 1 to 3 carbon atoms which is optionally substituted with a group of formula $—N^+(R^7)_3$ wherein each group $R^7$ is the same or different and is an alkyl group having from 1 to 3 carbon atoms.

Preferably, $R^4$, $R^5$, $R^{4'}$ and $R^{5'}$ are the same or different and each is selected from the group consisting of hydrogen atoms, alkyl groups having from 1 to 10 carbon atoms, alkoxy groups having from 1 to 10 carbon atoms and alkyl groups having from 1 to 10 carbon atoms (e.g. methyl groups) which are substituted with a substituent selected from the group consisting of aryl groups, heteroaryl groups, fluorenyl groups and spirobifluorenyl groups, said aryl, heteroaryl, fluorenyl and spirobifluorenyl groups being substituted (preferably at a position para to the alkyl group) with a disubstituted amino group the substituents of which are the same or different and are selected from the group consisting of aryl groups, heteroaryl groups, fluorenyl groups and spirobifluorenyl groups; more preferably, $R^4$, $R^5$, $R^{4'}$ and $R^{5'}$ are the same or different and each is selected from the group consisting of hydrogen atoms, alkyl groups having from 1 to 3 carbon atoms and alkoxy groups having from 5 to 10 carbon atoms; and most preferably, each of $R^4$, $R^5$ or $R^{4'}$ and $R^{5'}$ is a hydrogen atom or $R^4$ or $R^{4'}$ represents a hydrogen atom and $R^5$ or $R^{5'}$ represents an alkoxy group having from 7 to 10 carbon atoms.

Preferably, $R^6$ represents a hydrogen atom or an alkyl group having from 1 to 6 carbon atoms; and most preferably a hydrogen atom or an alkyl group having from 1 to 3 carbon atoms.

Preferred examples of the repeat unit of formula (III) are those wherein m and n are each 0 and X is a linking unit of formula -A-B-C- wherein:

(i) A and C each represent a methylene group and B is selected from the group consisting of O, S, $SO_2$, $NR^3$, $N^+(R^{3'})(R^{3''})$ and $C(R^4)(R^5)$ wherein $R^3$, $R^{3'}$, $R^{3''}$, $R^4$, $R^5$ and $R^6$ are as defined in the above definition of the repeat unit of formula (III);

(ii) A and C each represent a methylene group and B is selected from the group consisting of O, S, $SO_2$, $NR^3$ wherein $R^3$ is selected from the group consisting of hydrogen atoms and alkyl groups having from 1 to 6 carbon atoms which are optionally substituted with a group of formula —$N^+(R^7)_3$ wherein each group $R^7$ is the same or different and is selected from the group consisting of hydrogen atoms and alkyl groups having from 1 to 6 carbon atoms, $N^+(R^{3'})(R^{3''})$ wherein $R^{3'}$ and $R^{3''}$ are the same or different and each represents an alkyl group having from 1 to 6 carbon atoms which is optionally substituted with a group of formula —$N^+(R^7)_3$ wherein each group $R^7$ is the same or different and is selected from the group consisting of hydrogen atoms and alkyl groups having from 1 to 6 carbon atoms, and $C(R^4)(R^5)$ wherein $R^4$ and $R^5$ are the same or different and each is selected from the group consisting of hydrogen atoms, alkyl groups having from 1 to 10 carbon atoms, alkoxy groups having from 1 to 10 carbon atoms and alkyl groups having from 1 to 10 carbon atoms (e.g. methyl groups) which are substituted with a substituent selected from the group consisting of aryl groups, heteroaryl groups, fluorenyl groups and spirobifluorenyl groups, said aryl, heteroaryl, fluorenyl and spirobifluorenyl groups being substituted (preferably at a position para to the alkyl group) with a disubstituted amino group the substituents of which are the same or different and are selected from the group consisting of aryl groups, heteroaryl groups, fluorenyl groups and spirobifluorenyl groups;

(iii) A and C each represent a methylene group and B is selected from the group consisting of O, S, $SO_2$, $N^+(R^{3'})(R^{3''})$ wherein $R^{3'}$ and $R^{3''}$ are the same or different and each represents an alkyl group having from 1 to 3 carbon atoms which is optionally substituted with a group of formula —$N^+(R^7)_3$ wherein each group $R^7$ is the same or different and is an alkyl group having from 1 to 3 carbon atoms, and $C(R^4)(R^5)$ wherein $R^4$ and $R^5$ are the same or different and each is selected from the group consisting of hydrogen atoms, alkyl groups having from 1 to 3 carbon atoms and alkoxy groups having from 5 to 10 carbon atoms, particularly wherein each of $R^4$ and $R^5$ is a hydrogen atom or $R^4$ represents a hydrogen atom and $R^5$ represents an alkoxy group having from 7 to 10 carbon atoms;

(iv) A and C each represent O or S and B is selected from the group consisting of O, S, $SO_2$, $NR^3$, $N^+(R^{3'})(R^{3''})$ and $C(R^4)(R^5)$ wherein $R^3$, $R^{3'}$, $R^{3''}$, $R^4$, $R^5$ and $R^6$ are as defined in the above definition of the repeat unit of formula (III);

(v) A and C each represent O or S and B is a group of formula $C(R^4)(R^5)$ wherein $R^4$ and $R^5$ are the same or different and each represents a hydrogen atom or an alkyl group having from 1 to 10 carbon atoms; or (vi) A and C each represent O and B is a group of formula $C(R^4)(R^5)$ wherein $R^4$ and $R^5$ are the same or different and each represents an alkyl group having from 1 to 3 carbon atoms.

Particularly preferred repeat units are selected from the following group:

Selection of Repeat Units 1–11

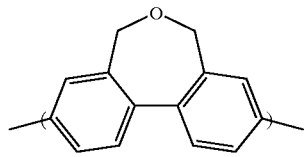

1

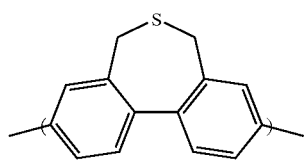

2

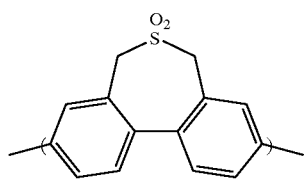

3

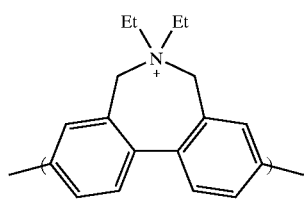

4

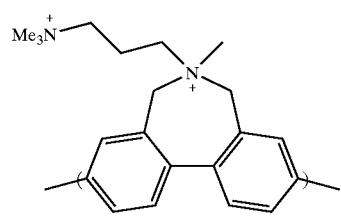

5

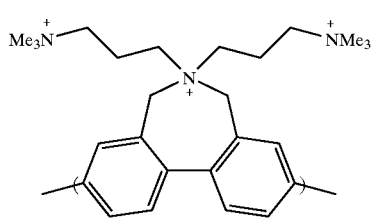

6

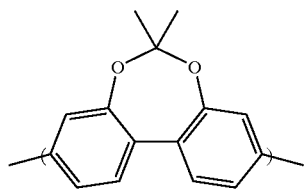

7

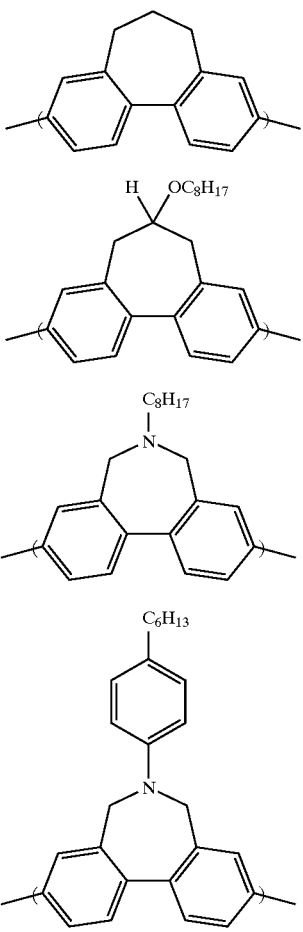

Many of the semiconductive polymers used in the optical devices of the present invention are novel. Therefore, in a further aspect of the present invention, there is provided a semiconductive copolymer in which one of the repeat units is a group of formula (II) as defined above or a semiconductive homopolymer in which the repeat unit is a group of formula (II) as defined above, with the proviso that, where $Y^1$ and $Y^2$ each represent a single bond, X may not represent a linking unit selected from the group consisting of —CO—O—CO—, —CO—NH—CO— and —O—P(O)(OH)—O—, and where $Y^1$ represents a phenyl group which is fused with the phenyl group to which it is attached to form a naphthalenyl group and $Y^2$ represents a phenyl group which is fused with the phenyl group to which it is attached to form a naphthalenyl group, X may not represent a group of formula —O—CH$_2$—O—.

Preferably, the semiconductive polymer of the present invention is a copolymer in which one of the repeat units is a group of formula (III) as defined above or a homopolymer in which the repeat unit is a group of formula (III) as defined above, with the proviso that, where $Y^1$ and $Y^2$ each represent a single bond, X may not represent a linking unit selected from the group consisting of —CO—O—CO—, —CO—NH—CO— and —O—P(O)(OH)—O—. The preferred, more preferred and most preferred options for substituents $R^3$, $R^{3'}$, $R^{3''}$, $R^4$, $R^5$, $R^6$ and $R^7$ and the linking unit -A-B-C- in the repeat unit of formula (III) of the copolymers and homolpolymers of the invention are as recited above for the optical devices of the present invention.

Preferably, the polymers used in the optical devices of the present inventions are copolymers or terpolymers. These copolymers include alternating AB copolymers and terpolymers, and statistical copolymers and terpolymers. These can be depicted by the following general formulae (IV), (V), (VI) and (VII):

 (IV)

 (V)

 (VI)

 (VII)

wherein:

(I) is a repeat unit as defined above, $D^1$, $D^2$ and $D^3$ are repeat units which are conjugated with the adjacent units in the polymer chain, $n^1$ is an integer greater than 3, the ratio of x:y is from 99:1 to 1:99, and the ratio of x:(y+z) is from 99:1 to 1:99.

The repeat units $D^1$, $D^2$ and $D^3$ are any conjugated units commonly used in electroluminescent polymers, e.g. those disclosed in Burroughes et al., Nature, 1990, 347, 539; WO-A-93/14177; WO-A-94/29883; U.S. Pat. No. 5,514,878; WO-A-99/54385; U.S. Pat. No. 5,672,678; WO-A-00/55927; EP-A-0707020; and co-pending application PCT/GB00/04594. Specific examples include the following conjugated units of formulae (VIII), (IX), (X), (XI), (XII), (XIII), (XIV) and (XV):

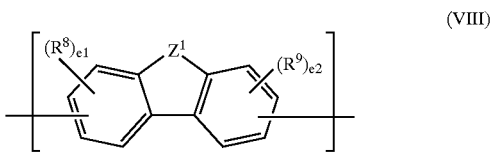 (VIII)

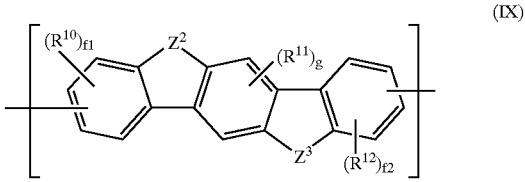 (IX)

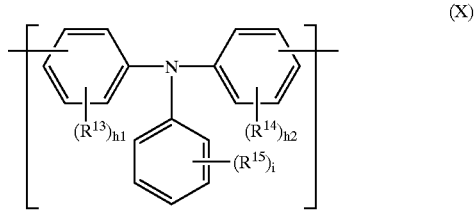 (X)

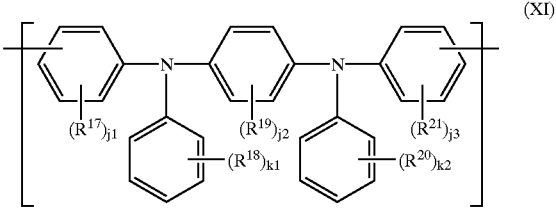 (XI)

-continued

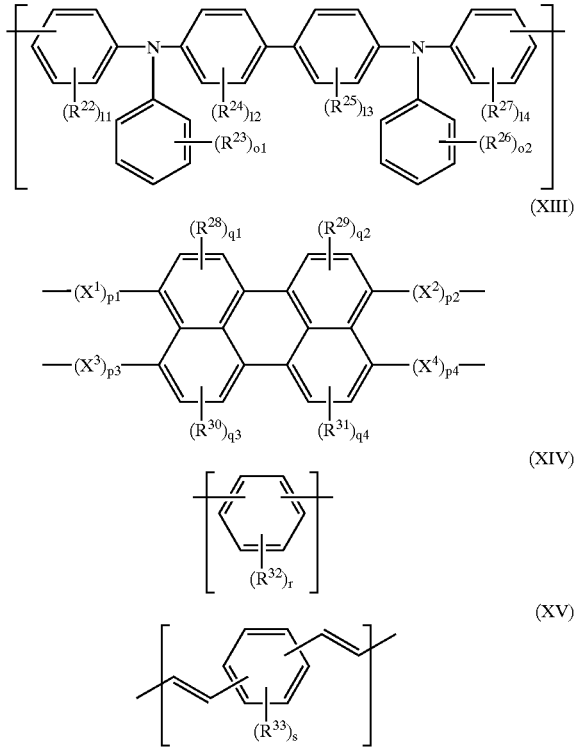

(XII)

(XIII)

(XIV)

(XV)

wherein:
each of $R^8$ to $R^{15}$ and $R^{17}$ to $R^{33}$ is the same or different and is selected from the group consisting of alkyl groups as defined above, haloalkyl groups as defined above, alkoxy groups as defined above, alkoxyalkyl groups as defined above, aryl groups as defined above, aryloxy groups as defined above, aralkyl groups as defined above and groups of formula —$COR^{16}$ wherein $R^{16}$ is selected from the group consisting of hydroxy groups, alkyl groups as defined above, haloalkyl groups as defined above, alkoxy groups as defined above, alkoxyalkyl groups as defined above, aryl groups as defined above, aryloxy groups as defined above, aralkyl groups as defined above, amino groups, alkylamino groups the alkyl moiety of which is as defined above, dialkylamino groups wherein each alkyl moiety is the same or different and is as defined above, aralkyloxy groups the aralkyl moiety of which is as defined above and haloalkoxy groups comprising an alkoxy group as defined above which is substituted with at least one halogen atom;

each of $Z^1$, $Z^2$ and $Z^3$ is the same or different and is selected from the group consisting of O, S, SO, $SO_2$, $NR^3$, $N^+(R^{3'})(R^{3''})$, $C(R^4)(R^5)$, $Si(R^{4'})(R^{5'})$ and $P(O)(OR^6)$, wherein $R^3$, $R^{3'}$, $R^{3''}$, $R^4$, $R^5$, $R^{4'}$, $R^{5'}$ and $R^6$ are as defined above;

each of $X^1$, $X^2$, $X^3$ and $X^4$ is the same or different and is selected from:
  aryl moieties as defined above;
  straight or branched-chain alkylene groups having from 1 to 6 carbon atoms;
  straight or branched-chain alkenylene groups having from 2 to 6 carbon atoms; and
  straight or branched-chain alkynylene groups having from 1 to 6 carbon atoms; or $X^1$ and $X^2$ together and/or $X^3$ and $X^4$ together can represent a linking group of formula (V) below:

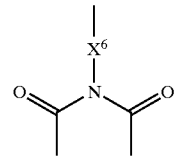

(V)

wherein $X^5$ represents an aryl moiety as defined above;
each of e1, e2, f1 and f2 is the same or different and is 0 or an integer of 1 to 3;
each of g, q1, q2, q3 and q4 is the same or different and is 0, 1 or 2;
each of h1, h2, j1, j2, j3, l1, l2, l3, l4, r and s is the same or different and is 0 or an integer of 1 to 4;
each of i, k1, k2, o1 and o2 is the same or different and is 0 or an integer of 1 to 5; and
each of p1, p2, p3 and p4 is 0 or 1.

In the above alternating AB copolymers and terpolymers, and statistical copolymers and terpolymers of general formulae (IV), (V), (VI) and (VII), the following are preferred:
(A) those wherein the repeat unit (I) is a repeat unit of formula (II) as defined above;
(B) those wherein the repeat unit (I) is a repeat unit of formula (III) as defined above;
(C) those wherein the repeat unit (I) is one of the preferred, more preferred and most preferred units of formula (III) described above;
(D) those wherein the repeat units $D^1$, $D^2$ and $D^3$ are selected from the group consisting of units of formulae (VIII), (IX), (XIV) and (XV) as defined above;
(E) those wherein the repeat unit $D^1$, $D^2$ or $D^3$ is a unit of formula (VIII) wherein $Z^1$, $Z^2$ and $Z^3$ are selected from the group consisting of O, S and $C(R^4)(R^5)$ wherein $R^4$ and $R^5$ are as defined above;
(F) those wherein the repeat unit $D^1$, $D^2$ or $D^3$ is a unit of formula (VIII) wherein each of e1 and e2 is 0 and $Z^1$, $Z^2$ or $Z^3$ is a group of formula $C(R^4)(R^5)$ wherein $R^4$ and $R^5$ are the same or different and are selected from the group consisting of hydrogen atoms, alkyl groups having from 1 to 10 carbon atoms (e.g. n-hexyl, n-octyl, 2-ethylhexyl and 3,7-dimethyloctyl groups) and alkyl groups having from 1 to 10 carbon atoms (e.g. methyl groups) which are substituted with a substituent selected from the group consisting of aryl groups, heteroaryl groups, fluorenyl groups and spirobifluorenyl groups, said aryl, heteroaryl, fluorenyl and spirobifluorenyl groups being substituted (preferably at the para position) with a disubstituted amino group the substituents of which are the same or different and are selected from the group consisting of aryl groups, heteroaryl groups, fluorenyl groups and spirobifluorenyl groups;
(G) those wherein the repeat unit $D^1$, $D^2$ or $D^3$ is a unit of formula (XV) having the following formula:

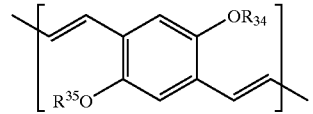

wherein $R^{34}$ and $R^{35}$ are the same or different and each is an alkyl group as defined above;
(H) statistical copolymers of formula (VI) wherein the ratio x:y is from 10:90 to 50:50;
(I) statistical copolymers of formula (VI) wherein the ratio x:y is from 10:90 to 45:55.

Of these, preferred are those alternating AB copolymers and terpolymers, and statistical copolymers and terpolymers of general formulae (IV), (V), (VI) and (VII) wherein the repeat unit (I) is as defined in (A) and the repeat units $D^1$, $D^2$ and $D^3$ are as defined in (D); more preferred are those alternating AB copolymers and terpolymers, and statistical copolymers and terpolymers of general formulae (IV), (V), (VI) and (VII) wherein the repeat unit (I) is as defined in (B) and the repeat units $D^1$, $D^2$ and $D^3$ are as defined in (E) or (G); yet more preferred are those alternating AB copolymers and terpolymers, and statistical copolymers and terpolymers of general formulae (IV), (V), (VI) and (VII) wherein the repeat unit (I) is as defined in (C) and the repeat units $D^1$, $D^2$ and $D^3$ are as defined in (E) or (G); particularly preferred are those alternating AB copolymers and terpolymers, and statistical copolymers and terpolymers of general formulae (IV), (V), (VI) and (VII) wherein the repeat unit (I) is as defined in (C) and the repeat units $D^1$, $D^2$ and $D^3$ are as defined in (F) or (G); and most preferred are the statistical copolymers of formula (VI) as defined in (H) wherein the repeat unit (I) is as defined in (C) and the repeat unit $D^1$ is as defined in (F) or (G).

The optical devices of the present invention may comprise a semiconductive polymer of the present invention alone supported by a substrate or the semiconductive polymer of the present invention may be blended with further semiconductive polymers, for example as disclosed in WO-A-99/48160.

The semiconductive polymers used in the preparation of the optical devices of the present invention can be prepared using any of the polymerisations provided by the standard families of polycondensation techniques (e.g. Heck, Suzuki, Yamamoto, Horner, Wessling and Gilch polycondensation techniques; see U.S. Pat. No. 5,777,070 and the review article "Electroluminescent Conjugated Polymers—Seeing Polymers in a New Light", A. Kraft, A. C. Grimsdale and A. B. Holmes, *Angew. Chem. Int. Ed. Engl.*, 1998, 37, 402–428, the contents of which are incorporated herein by reference thereto). The choice of the desired monomers and the suitable polycondensation techniques can be made by the person skilled in this field depending upon the nature of the target semiconductive polymer of the present invention.

One of the preferred techniques due to its simplicity and flexibility is the Suzuki reaction. Thus, the polymers of the present invention may be synthesised according to the Scheme 1 below:

Scheme 1

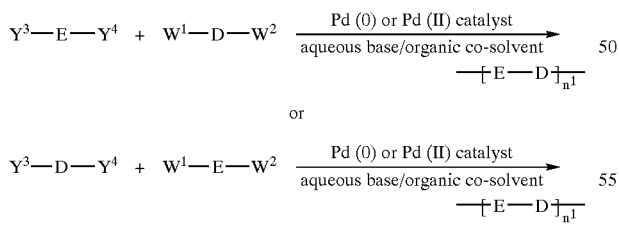

wherein:
E is a repeat unit of formula (I), (II) or (III) as defined above;
D is a repeat unit of formula $D^1$, $D^2$ or $D^3$ as defined above;
$Y^3$ and $Y^4$ are leaving groups;
$W^1$ and $W^2$ are selected from the group consisting of boronic acid groups [$B(OH)_2$], boronate ester groups of formula $B(OR^{35})_2$ wherein $R^{35}$ is selected from the group consisting of alkyl groups as defined above and aryl groups as defined above or the two $R^{35}$ groups together represent a straight or branched chain alkylene group having from 2 to 10 carbon atoms, and boranes of formula $B(OR^{36})_2$ wherein $R^{36}$ is selected from the group consisting of alkyl groups as defined above, aryl groups as defined above and aralkyl groups as defined above; and
$n^1$ is an integer greater than 3.

Typically, in the above, the leaving groups $Y^3$ and $Y^4$ may be bromine or iodine; the substituents $W^1$ and $W^2$ may be boronate ester groups of formula $B(OR^{35})_2$ wherein the two groups $R^{35}$ together represent an alkylene group having from 2 to 6 carbon atoms such as a 2,3-dimethylbutylene group; the palladium catalyst may be tetrakis-(triphenylphosphine)palladium (0); the base may be tetraalkylammonium hydroxide, most preferably tetraethylammonium hydroxide as described in WO 00/53656, PCT/GB00/00771; the reaction may be performed in toluene containing sodium carbonate as the required base and Aliquat® as a phase-transfer catalyst.

Scheme 2 below shows two specific examples of a Suzuki polymerisation of the general type set out in Scheme 1 above.

Scheme 2

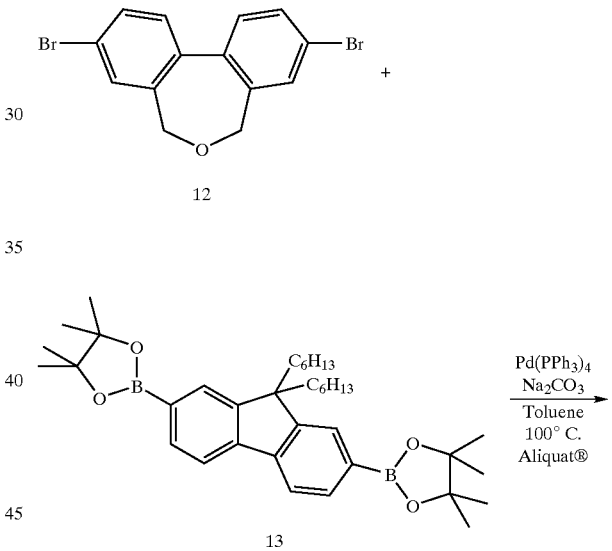

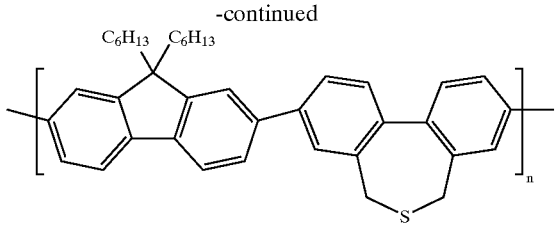

16

As already noted above, we particularly prefer statistical semiconductive copolymers comprising repeat units of formulae (I) and $D^1$. We have discovered a preferred method of synthesising such statistical copolymers which is a variation of the Suzuki polymerisation technique which enables the introduction of precise amounts of the repeat unit of formula (I) in a truly random manner along the polymer backbone. This has application not only in the present invention but also to the synthesis of other random statistical conjugated polymers.

Thus, in a further aspect of the present invention, there is provided a process for the preparation of a random statistical conjugated polymer comprising reacting, in the presence of a palladium (0) or palladium (II) catalyst and a base, $x^1$ moles of a monomer of formula $Y^5$-$F^1$-$Y^6$, $y^1$ moles of $W^3$-$F^1$-$W^4$ and $z^1$ moles of a monomer of formula $W^5$-$G^1$-$W^6$, wherein $Y^5$ and $Y^6$ are leaving groups, $W^3$, $W^4$, $W^5$ and $W^6$ are selected from the group consisting of boronic acid groups [B(OH)$_2$], boronate ester groups of formula B(OR$^{35}$)$_2$ wherein R$^{35}$ is as defined above and boranes of formula B(OR$^{36}$)$_2$ wherein R$^{36}$ is as defined above, $F^1$ and $G^1$ are radicals the nature of which is such that, on polymerisation, the groups $F^1$ and $G^1$ in the resulting polymerisation product are conjugated, and the molar ratio $x^1:(y^1+z^1)$ is 1:1, to give a random statistical conjugated polymer of formula (XVI) below wherein $F^1$, $G^1$, $x^1$, $y^1$ and $z^1$ are as defined above, the molar ratio $(x^1+y^1):z^1$ being greater than 1:

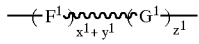

(XVI)

Typically, in the above, the leaving groups $Y^5$ and $Y^6$ may be bromine or iodine; the substituents $W^3$, $W^4$, $W^5$ and $W^6$ may each represent a boronate ester group of formula B(OR$^{35}$)$_2$ wherein the two groups R$^{35}$ in each boronate ester group together represent an alkylene group having from 2 to 6 carbon atoms such as a 2,3-dimethylbutylene group; the palladium catalyst may be tetrakis(triphenylphosphine) palladium (0); and the reaction may be performed in toluene containing sodium carbonate as the required base and Aliquat® as a phase-transfer catalyst. Preferably the palladium catalyst is combined with a tetraalkylammonium hydroxide base.

It has been surprisingly found that tricyclohexylphosphine in combination with palladium(II) acetate and tetraethylammonium hydroxide in toluene can lead to extremely rapid polymerisations and high molecular weight polymer. For the poly(9,9-dialkylfluorene-2,7-diyl) homopolymers typical $M_p$ (as measured by GPC) in the range 200,000–350,000 were attained. Tri(tert-butylphosphine) may also be used. These specific phosphines were described by A. F. Littke and G. C. Fu, *J. Am. Chem. Soc.*, 2001, 123, 6989 (and references cited therein) as suitable for efficient Suzuki coupling catalysts, but it is surprising that high molecular weight polymers are also accessible. Preferred stoichiometry includes 1 mol % palladium acetate, 3 mol % phosphines and 5 equivalents of tetraethylammonium hydroxide per mole of dibromoarene.

This modification of the Suzuki polymerisation technique is particularly useful as it enables truly random statistical copolymers to be formed in which small amounts of a desired monomer unit can be incorporated into the backbone of a polymer containing much larger amounts of the comonomer unit. In the specific example of the copolymers of the present invention, a copolymer of formula (VI) as defined above may be synthesised using the above method [in which method $G^1$ in the monomer $W^5$-$G^1$-$W^6$ is the repeat unit of formula (I) as defined above], said copolymer of formula (VI) having a molar proportion of the repeat unit $D^1$ which is much greater than that of the repeat unit of formula (I), allowing small amounts of twisting to be introduced along the polymer backbone. This random introduction of small amounts of the repeat unit (I) allows control over the degree of reduction of conjugation in the polymer produced by the introduction of said repeat unit of formula (I). As a consequence, the change in the HOMO-LUMO bandgap can be tailored as required to produce the desired blue-shift in the polymer emission, and the degree to which aggregation of the polymers is reduced can be similarly tuned.

A further example of a suitable polymerisation technique is a Horner-Emmons polycondensation of a phosphonate with an aldehyde, as illustrated below in Scheme 3.

Scheme 3

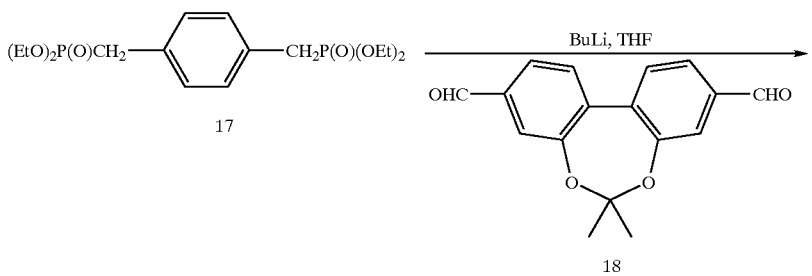

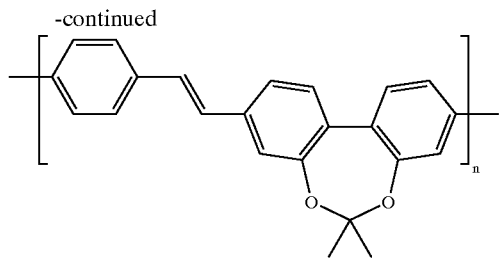

19

In the polymerisation techniques described above, end-capping units may be introduced if required, e.g. by the addition of aryl bromides or aryl boronates after a predetermined time to prevent further chain extension of the polymers.

The twisted monomers of the present invention of formulae $Y^3$-E-$Y^4$ and $W^1$-E-$W^2$ as defined above can be synthesised according to standard techniques well known in the field of synthetic organic chemistry. Examples of such techniques are illustrated in the following Schemes 4 to 7.

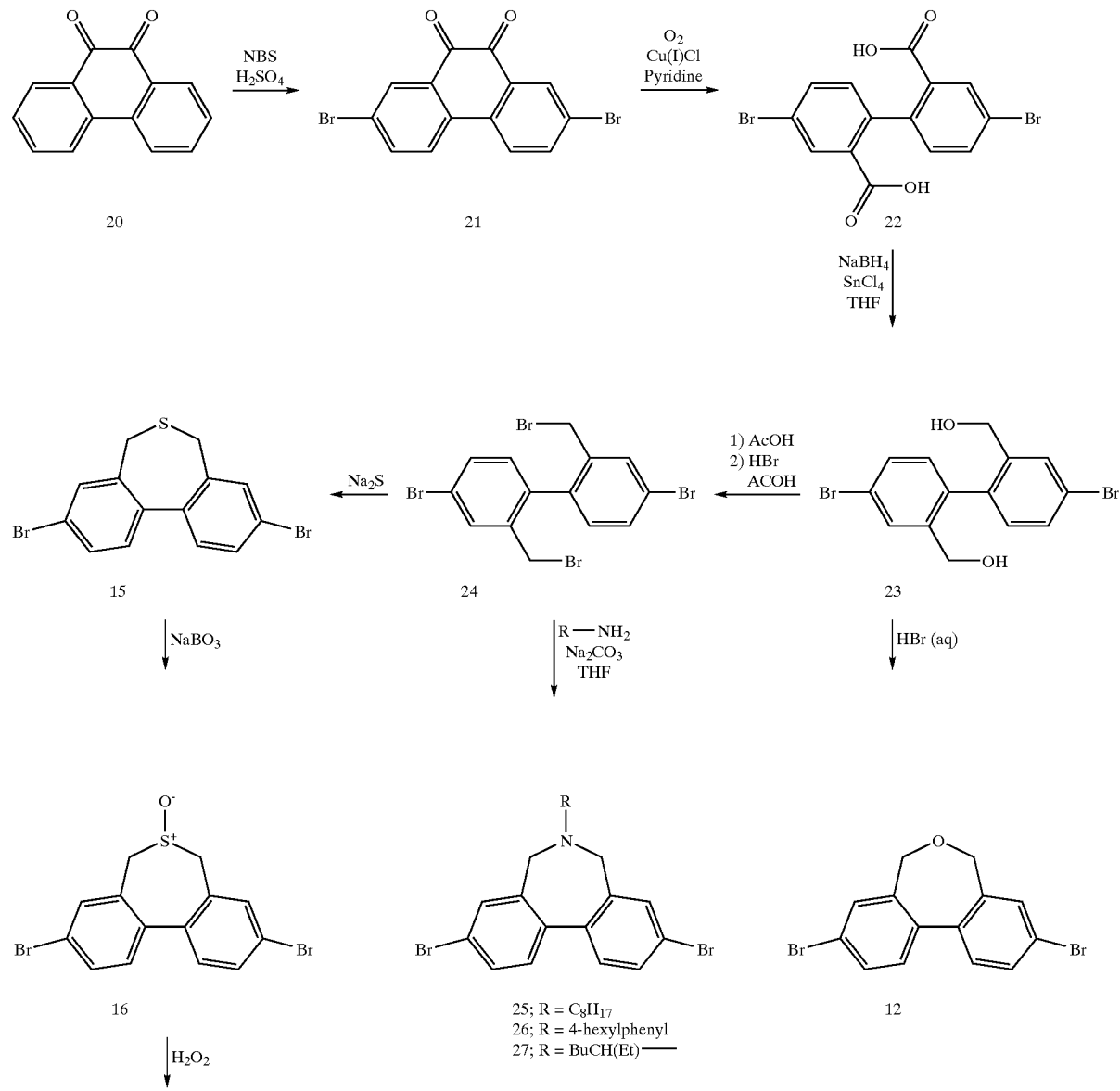

Scheme 4

-continued
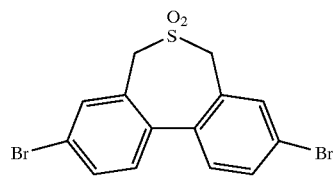
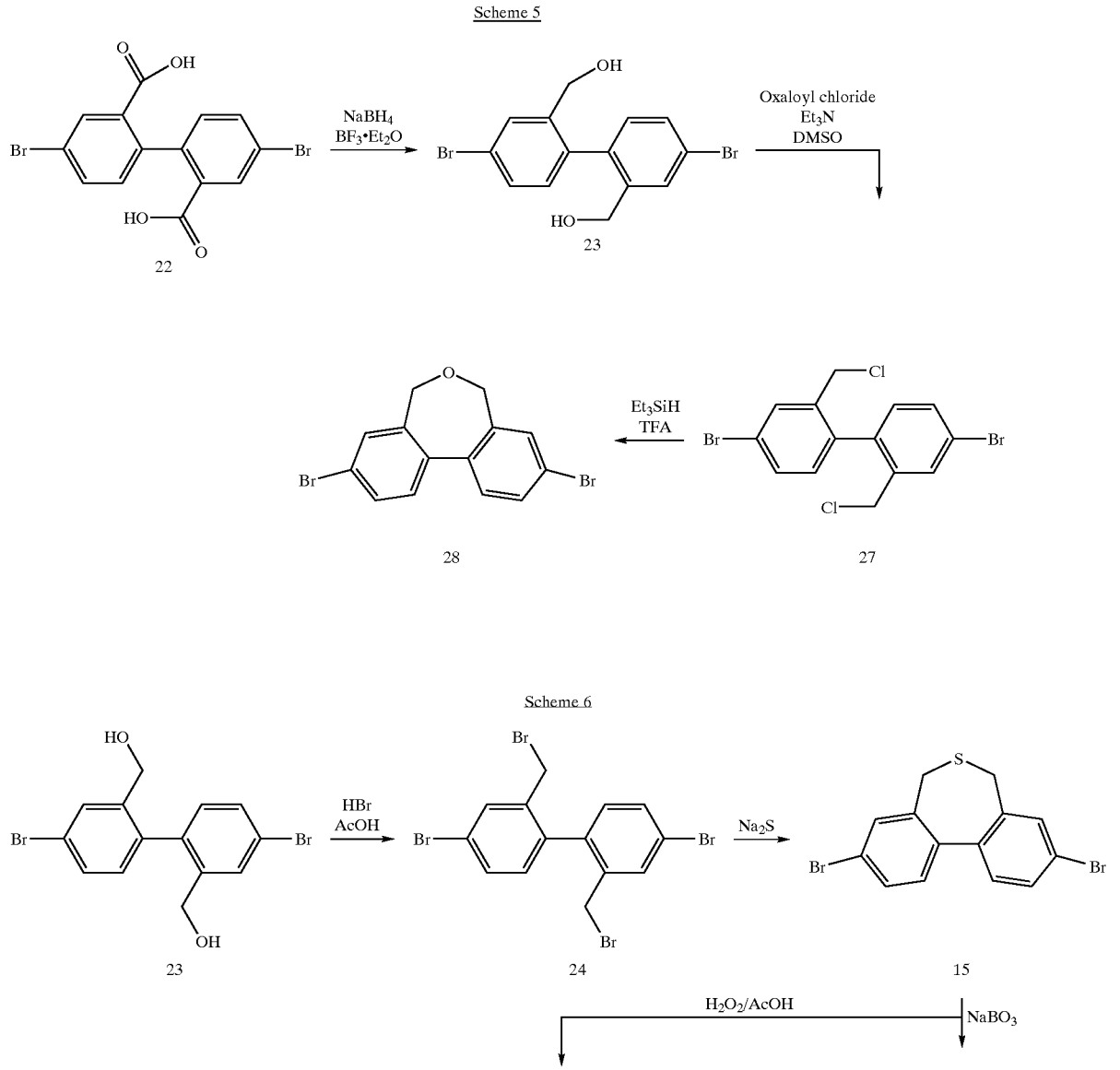
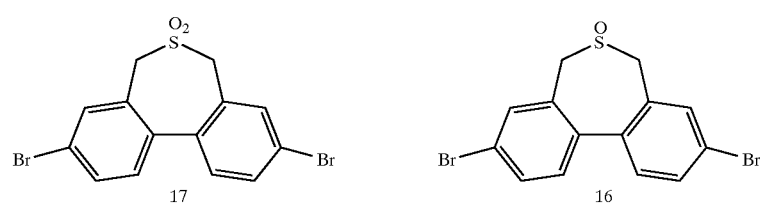

21

Scheme 7

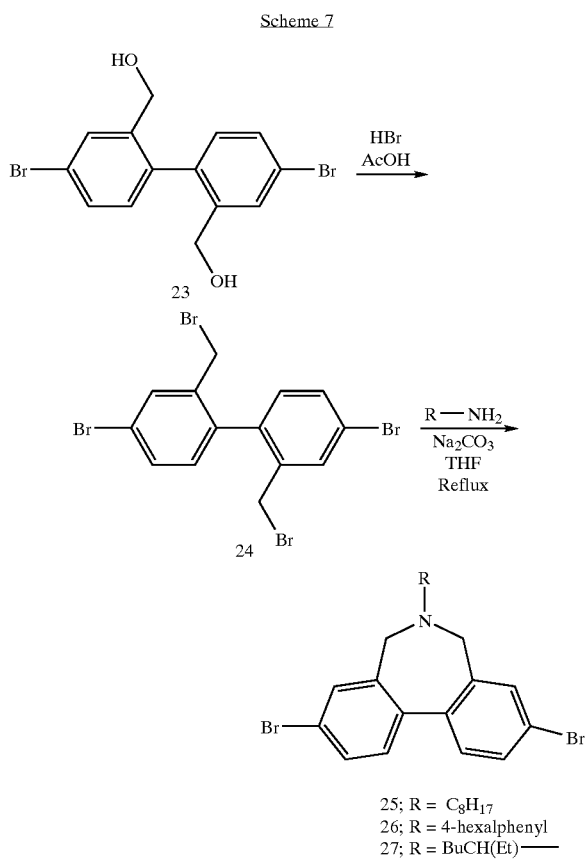

25; R = C$_8$H$_{17}$
26; R = 4-hexalphenyl
27; R = BuCH(Et)—

Many of the monomers used in the above polymerisation reactions are novel. In a further aspect of the present invention there are provided monomers of formulae $Y^3$-E-$Y^4$ and $W^1$-E-$W^2$, wherein E, $W^1$, $W^2$, $Y^3$ and $Y^4$ are as defined above, provided that, where each of $Y^3$ and $Y^4$ is a bromine atom, E does not represent a dibenzoxepinyl, dibenzothiepinyl, dibenzothiepinyl S-oxide or dibenzothiepinyl S,S-dioxide group.

The optical devices of the present invention may be prepared according to any method known in this field for the preparation of optical devices. Suitable preparation methods are disclosed in, for example, the following, the contents of which are incorporated herein by reference thereto: WO-A-90/13148; U.S. Pat. No. 5,512,654; WO-A-95/06400; R. F. Service, Science 1998, 279, 1135; Wudl et al., Appl. Phys. Lett. 1998, 73, 2561; J. Bharathan, Y. Yang, Appl. Phys. Lett. 1998, 72, 2660; and T. R. Hebner, C. C. Wu, D. Marcy, M. L. Lu, J. Sturm, Appl. Phys. Lett. 1998, 72, 519).

As an example, a typical thin-film LED optical device according to the present invention comprises O$_2$ plasma-treated ITO-coated glass, a poly(styrene sulfonate)-doped poly(3,4-ethylene dioxythiophene) (PEDOT:PSS) hole injection layer, a thin film of a semiconductive copolymer of the present invention, and a Ca—Al cathode. The PEDOT:PSS films (typically approximately 70 nm in thickness) can be spun from a filtered H$_2$O solution before heating to 100° C. under N$_2$ for 30 minutes. Spin-coating can also be also used to deposit the emissive copolymer films of the present invention (typically approximately 100 nm in thickness) from xylene solutions in a nitrogen-filled glove box. The Ca cathode (typically approximately 500 Å in thickness) and Al protective layers (typically approximately 150 Å in thickness) can be deposited by thermal evaporation in a vacuum (e.g. base pressure approximately 5×10$^{-6}$ mbar) patterned by a shadow mask.

Water soluble and polyelectrolyte copolymers according to the present invention may be prepared by the copolymerisation of ammonium salts with suitable fluorene monomers. Selection of suitable polymers could be advantageous for inkjet printing as well as layer by layer deposition of light emitting polyelectrolytes.

BRIEF DESCRIPTION OF THE DRAWINGS

The present invention may be further understood by consideration of the following embodiments of the present invention, with reference to the following drawings in which.

EXAMPLES

Example 1

Synthesis of 3,9-dibromo-5,7-dihydro-dibenz[c,e]oxepin (7)

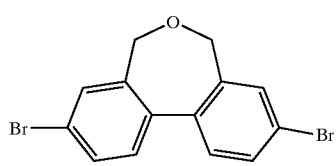

12

Figure 1:
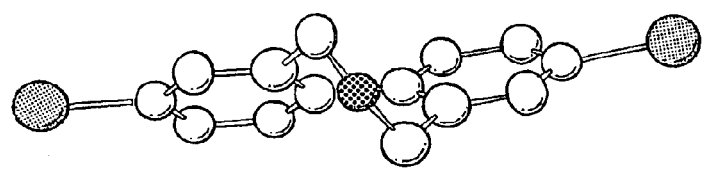
FIG. 1 shows the X-ray crystal structure of a twisted monomer 12 prepared in Example 1 below.

4,4'-Dibromo-2,2'-bis-hydroxymethyl-biphenyl 23, the structure of which is shown in Scheme 4 above, (5 g, 0.013 moles, prepared according to the procedure described by D. M. Hall, F. Minhaj, J. Chem. Soc., 1957, 4584) was dissolved in THF (50 ml). HBr (48% wt/wt aqueous solution, 40 ml) was added and the solution refluxed overnight. After this period the THF was removed under reduced pressure and the yellow oil extracted between DCM/H$_2$O (DCM is dichloromethane). The combined organic layers were dried (MgSO$_4$), reduced and recrystallised from acetone (100 ml) to yield 3,9-dibromo-5,7-dihydro-dibenz[c,e]oxepin (12) as fine white crystals (1 g). Repeated recrystallisations of the mother liquor gave further product. Total yield after 3 recrystallisations (2.2 g, 0.0062 moles, 48% yield) as fine white crystals.

$^1$H-NMR (400 MHz, CDCl$_3$): 4.30 (4H, s, CH$_2$), 7.39 (2H, d, ArH, J 8), 7.58–7.63 (4H, m, ArH); $^{13}$C-NMR (100 MHz, CDCl$_3$) 67.0, 122.4, 128.9, 132.1, 132.7, 136.8, 139.0; Elemental analysis (calculated for C$_{14}$H$_{10}$Br$_2$O, C, 47.50; H, 2.85%); found: C, 47.44; H, 2.94%;

mp. 129–131° C.

The X-ray crystal structure of 3,9-dibromo-5,7-dihydro-dibenz[c,e]oxepin (12) thus prepared was obtained using single crystal X-ray crystallography and this is shown in FIG. 1. From this it was possible to measure that there is a torsion angle about the biphenyl linkage of 41.25° between the phenyl rings.

Using similar synthetic methodology as described above for the preparation of 3,9-dibromo-5,7-dihydro-dibenz[c,e]oxepin, the further twisted monomers 15, 17, 25–32 shown below have been prepared. The torsion angle for many monomers has been measured as for 3,9-dibromo-5,7-dihydro-dibenz[c,e]oxepin, and the values are shown in brackets after each number. It should be noted that 29, 30, and 32 were not converted to the dibromo derivatives, but the potential for exploitation in cross-coupling reactions is evident.

Torsion angles from X-ray crystal structures of selected monomers

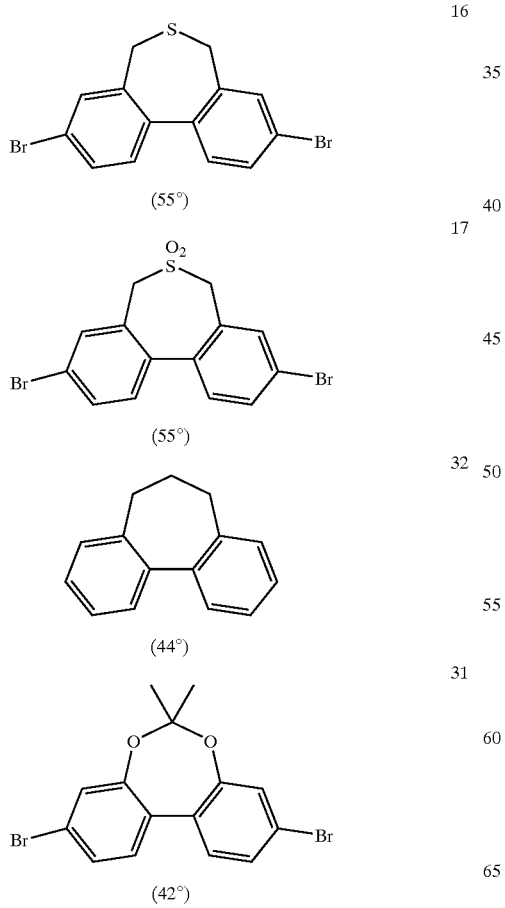

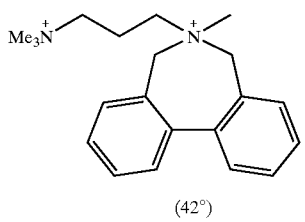

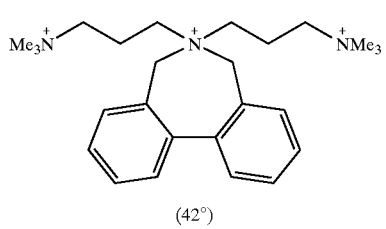

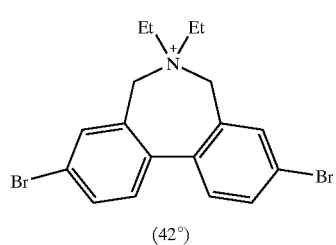

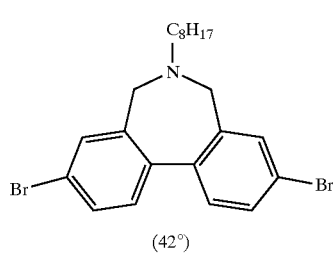

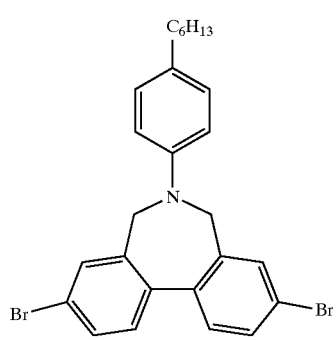

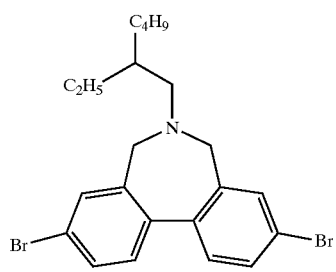

Example 2

Statistical Polymerisation of 3,9-dibromo-5,7-dihydro-dibenz[c,e]oxepin (12) with 9,9-di-n-hexylfluorene-2,7-bis-(isopropoxy-4,4,5,5-tetra-methyl-1,3,2-dioxaboronate) 13 and 2,7-dibromo-9,9-di-n-hexylfluorene 9,9-Di-n-hexylfluorene-2,7-bis-(isopropoxy-4,4,5,5-tetra-methyl-1,3,2-dioxaboronate) (structure 13 below) (1.84 g, 3.13 mmol), 2,7-dibromo-9,9-di-n-hexylfluorene (154 mg, 0.313 mmol) and 3,9-dibromo-5,7-dihydro-dibenz[c,e]oxepin 12 (1 g, 2.82 mmol), prepared as described in Example 1 above, were placed in a flame dried Schlenk tube under nitrogen. Tetrakis(triphenylphosphine)palladium (0) (40 mg, 0.03 mmol), toluene (40 ml), aqueous sodium carbonate (6 ml, 2 M) and Aliquat® (120 mg) were then added and the solution degassed. The resulting mixture was heated to 100° C. for 48 hours under nitrogen. The resulting viscous liquid was then precipitated in methanol to give an off-white solid. The polymer was finally re precipitated from a filtered toluene solution into methanol to give poly(9,9-dialkylfluorene)-co-(5,7-dihydro-dibenz[c,e]oxepin) (structure 33 below: 55% fluorene, and 45% structural unit derived from 12).

Conventional calibration GPC (PS standards, 30° C.) Mn 12 K, MWD 5, bimodal);

$^1$H-NMR (250 MHz, CDCl$_3$) 0.80 (br, 10H, CH$_3$+CH$_2$), 1.12 (br, 12H, CH$_2$), 2.12 (br, 4H, CH$_2$), 4.50 (br, 3.6H, CH$_2$, 45% of 4H CH$_2$ signal of methylene groups adjacent to the aromatic ring in hexyl substituents in relation to 4H signal at 2.12 ppm), 7.50–7.87 (12H, Ar—H);
Solution UV (methylenechloride, RT) $\lambda_{max}$ 366 nm;
Thin film UV $\lambda_{max}$ 372 nm;
Cylic voltammetry (Ag/AgCl corrected with iron (II) ferrocene) $E_{OX}$ 1.46 V, $E_{red}$ −0.84 V $E_{OX}$-$E_{red}$ 2.3 eV;
PL Spectra (methylene chloride) $\lambda_{max}$ 412 nm, $\lambda_{max}$ (shoulder) 445 nm;
PL spectra $\lambda_{max}$ 418 nm, $\lambda_{max}$ (shoulder) 450 nm.

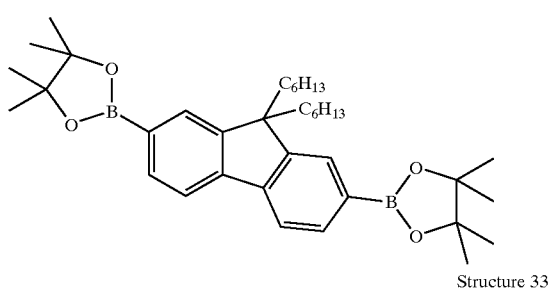

Structure 33

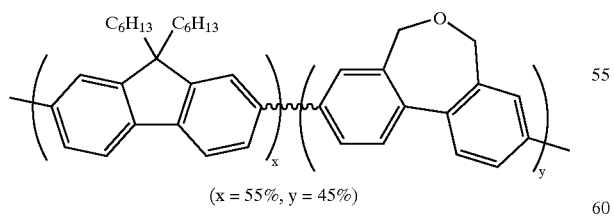

(x = 55%, y = 45%)

By varying the relative amounts of 9,9-di-n-hexylfluorene-2-(isopropoxy-4,4,5,5-tetra-methyl-1,3,2-dioxaboronate), 2,7-dibromo-9,9-di-n-hexylfluorene and 3,9-dibromo-5,7-dihydro-dibenz[c,e]oxepin used in the above polymerisation technique, a series of statistical copolymers shown in Table 1 below were prepared [the polymer having 0% of B is, of course, the homopolymer poly(di-n-hexylfluorene)].

TABLE 1

33

| Polymer Composition (%) | |
|---|---|
| A | B |
| 100 | 0 |
| 90 | 10 |
| 75 | 25 |
| 65 | 35 |
| 55 | 45 |
| 50 | 50 |

Figure 2:
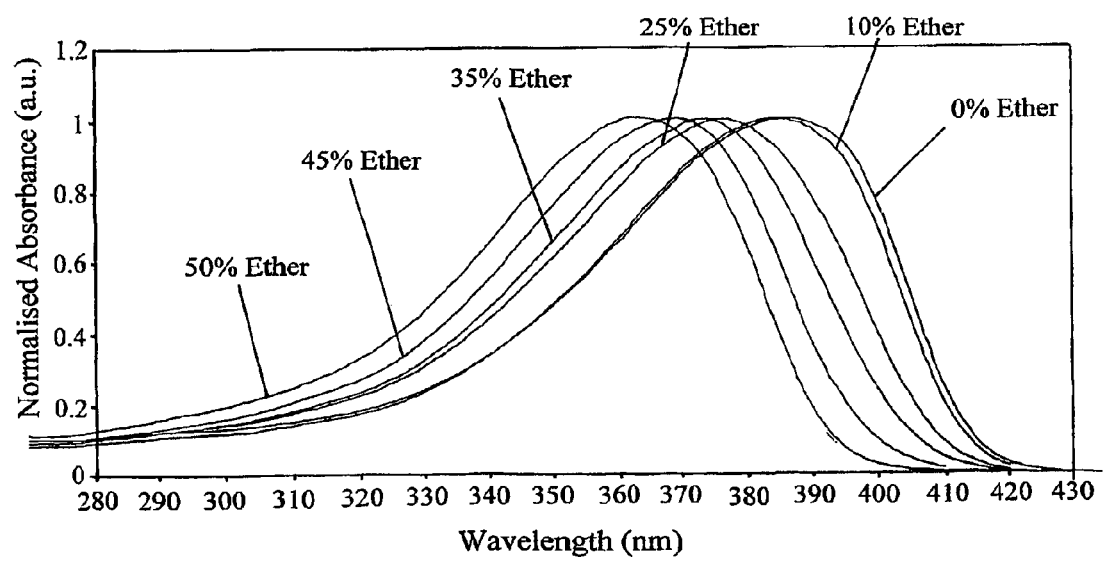
FIG. 2 shows UV/VIS solution spectra for various semi-conductive polymers of general formula 33 prepared in Example 2 below.

The solution UV/VIS absorption spectra of these polymers 33 were obtained and are illustrated in FIG. 2 (in this figure, the term "ether" refers to the twisted monomer unit of structure B in 33). As can be seen, a blue shifted emission was obtained in the copolymers of the present invention, the shift increasing with increasing amount of twisted monomer unit of structure B.

Figure 3:
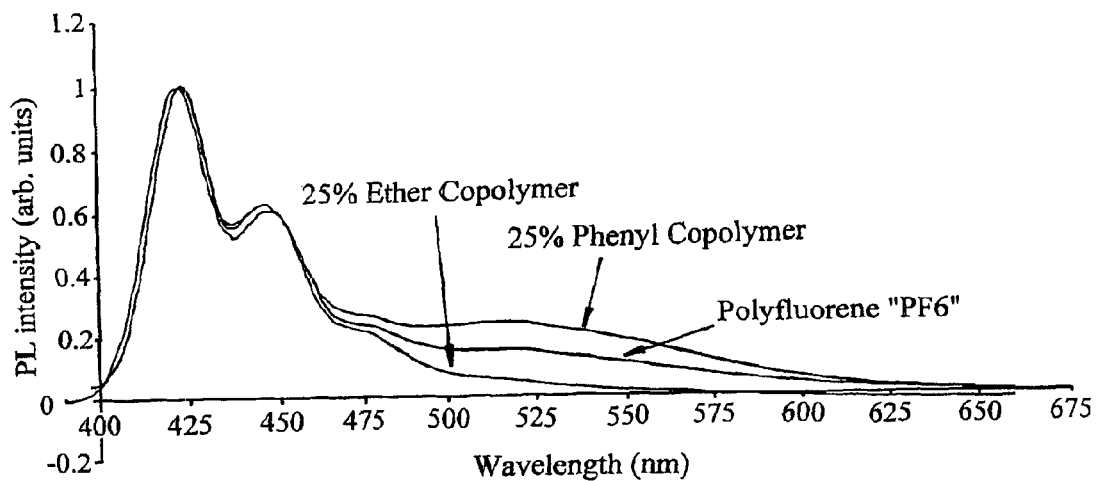
FIG. 3 shows thin film photoluminescence spectra for a semiconductive polymer of general formula 33 prepared in Example 2 below and two prior art copolymers.

The UV/VIS absorption spectra for the statistical copolymer of formula 33 having 25% of unit B and 75% of unit A was compared with the spectra for poly (di-n-hexylfluorene) having the structure 34 below and a copolymer having the structure 35 below containing 75% 9,9-di-n-hexylfluorenyl groups and 25% phenyl groups (see FIG. 3). As can be seen, the statistical copolymer of the present invention has a considerably reduced long wavelength tail in the visible region when compared with the two prior art polymers.

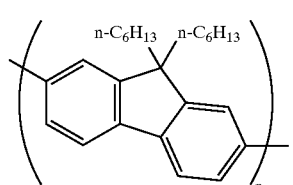

34

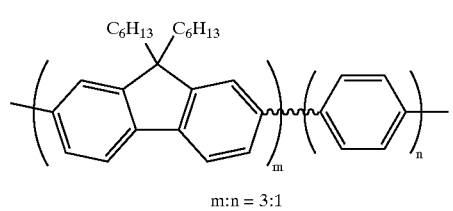

35 m:n = 3:1

Figure 4:
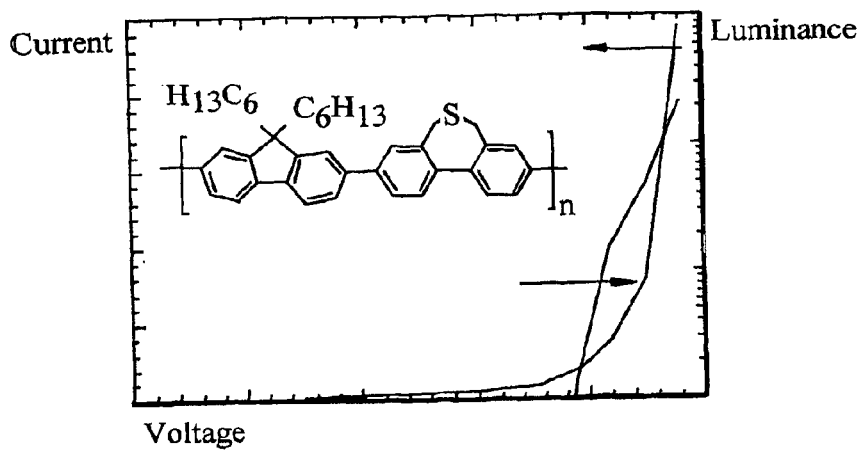
FIG. 4 shows a current-voltage photoluminescence curve for a two layer electroluminescent device incorporating a semiconductive statistical copolymer of formula 36 prepared in Example 3 below.
Figure 5:
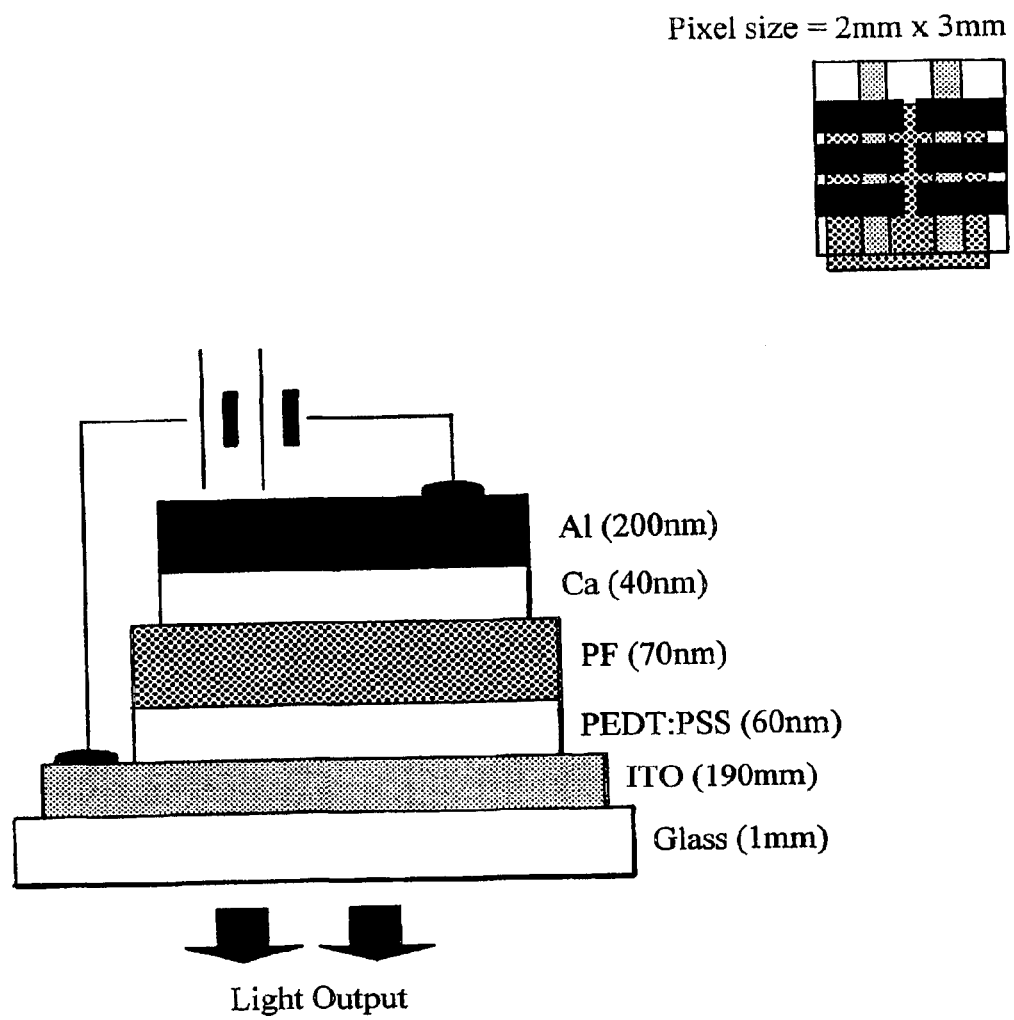
FIG. 5 shows a schematic diagram of an electroluminescent device of the present invention.

The photoluminescence spectra of the copolymers of this example were measured and are shown in FIG. 4 (in dichloromethane) and FIG. 5 (thin film). As the amount of 5,7-dihydro-dibenz[c,e]oxepin decreases, the emission is shifted to longer wavelength. Additionally, cyclic voltammetry data for the copolymers were measured, the results of which are as follows.

| Polymer | Eox (V) | Ered (V) | Band Gap (eV) | Homo (eV) | Lumo (eV) |
|---|---|---|---|---|---|
| PF6 | 1.36 | −0.91 | 2.3 | −6.2 | −3.9 |
| 10% B | 1.33 | −0.97 | 2.3 | −7.5 | −3.8 |
| 25% B | 1.34 | −0.93 | 2.3 | −6.1 | −3.9 |
| 35% B | 1.54 | −0.89 | 2.4 | −6.3 | −3.9 |
| 45% B | 1.46 | −0.84 | 2.3 | −6.3 | −4.0 |
| 50% B | 1.47 | −0.82 | 2.3 | −6.3 | −4.0 |

1 40 mV/s sweep rate
2 MeCN solvent, 0.1 M tetraalkylammonium tetrafluoroborate electrolyte
3 Polymers studied as thin films spun from toluene solution
4 This band gap corresponds to light of wavelength 540 nm (green)
5 Values are against Ag/AgCl corrected with FOC (0.43 V)

Example 3

Statistical Polymerisation of 3,9-dibromo-5,7-dihydro-dibenz[c,e]thiepin (15) with 9,9-di-n-hexylfluorene-2,7-bis-(isopropoxy-4,4,5,5-tetra-methyl-1,3,2-dioxaboronate) 13

To a solution of 3,9-dibromo-5,7-dihydro-dibenz[c,e]thiepin 15 (0.37 g, 1.00 mmol, 1 equivalent) and 9,9-di-n-hexylfluorene-2,7-bis-(isopropoxy-4,4,5,5-tetra-methyl-1,3,2-dioxaboronate) 13 (0.50 g, 1.00 mmol, 1 eq.) in dry degassed tetrahydrofuran (30 ml) (degassing was achieved by three pump-freeze-thaw cycles) was added a solution of $Cs_2CO_3$ (3.3 g in 5 ml $H_2O$, 2 M) and tetrakis(triphenylphosphine)palladium(0) (0.021 g, 0.02 mmol, 0.02 equivalents) under an atmosphere of nitrogen. After heating to reflux for 4 days, the concentrated polymer solution was filtered through a short silica plug (pasteur pipette) and then precipitated from methanol (500 ml). After drying the title polymer 36 was obtained in 32% yield as a white solid (0.18 g); $v_{max}$ ($CHCl_3$)/cm$^{-1}$ 3037, 2931, 2860, 2393, 1605, 1465, 1262, 1003, 820; $\delta_H$ (500 MHz; $CDCl_3$): 7.85–7.38 (12H, m, ArH), 3.76 (2H, br s, $SCH_2$), 3.52 (2H, br s, $SCH_2$), 2.10 (4H, br s, $ArC(CH_2C_5H_{11})_2$), 1.22–1.05(12H, br s, alkyl), 0.83–0.64 (10H, m, alkyl); GPC ($CHCl_3$) $M_w$ 1.4·10$^4$, $M_n$ 4.3·10$^3$, $M_w/M_n$ 3.3; TGA: 391° C. (5% weight loss); $\lambda_{max}$ ($CHCl_3$)/nm 356.

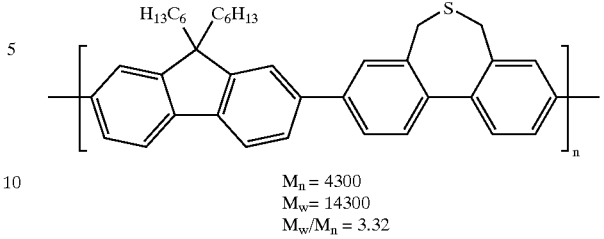

$M_n$ = 4300
$M_w$ = 14300
$M_w/M_n$ = 3.32

Example 4

Preparation of an Electroluminescent Device

Figure 7:
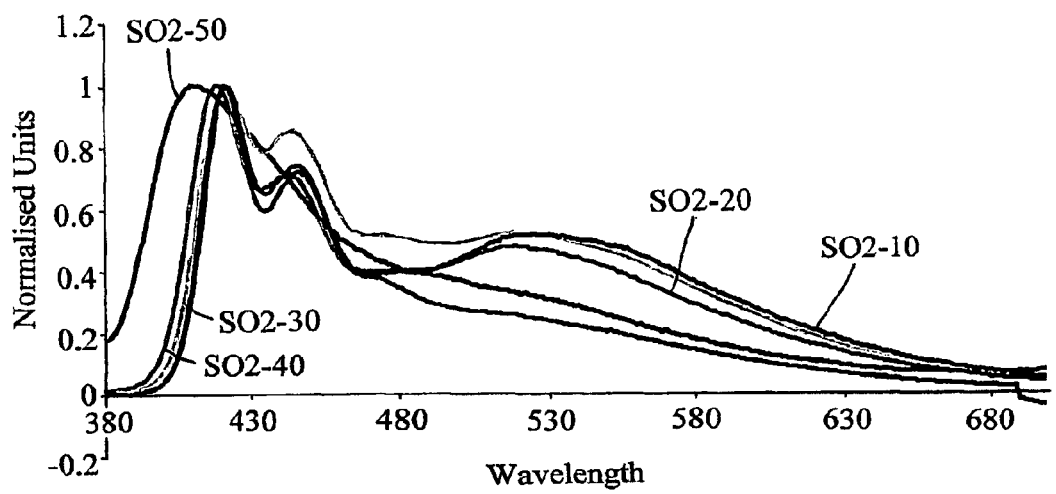
FIG. 7 Thin film photoluminescence spectra for the designated copolymers (excitation wavelength 360 nm).
Figure 7:
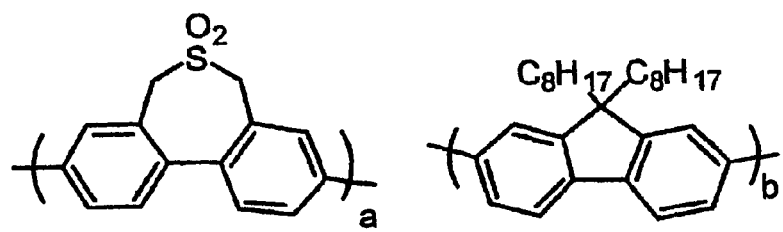
Figure 8:
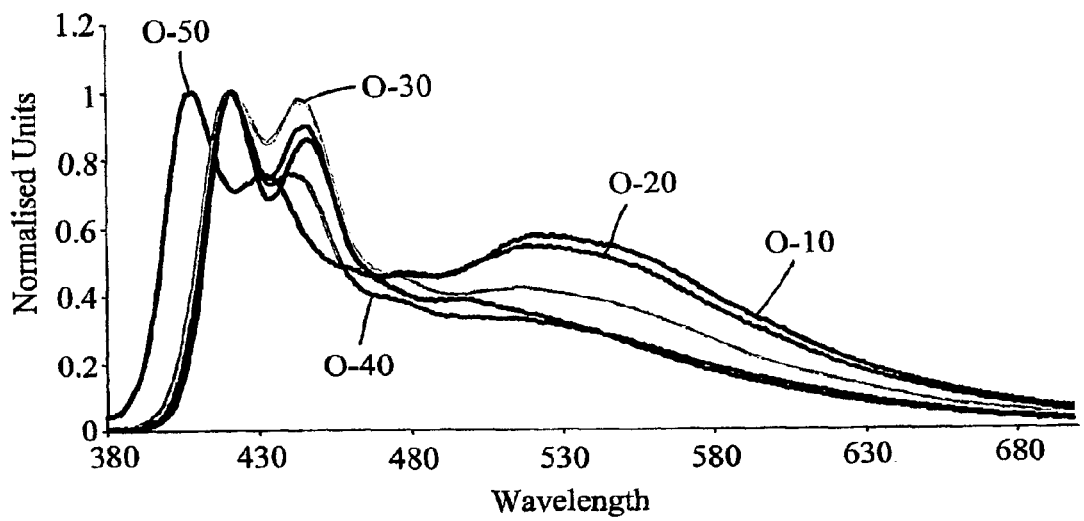
FIG. 8 Thin film photoluminescence spectra for the designated copolymers (excitation wavelength 360 nm).
Figure 8:
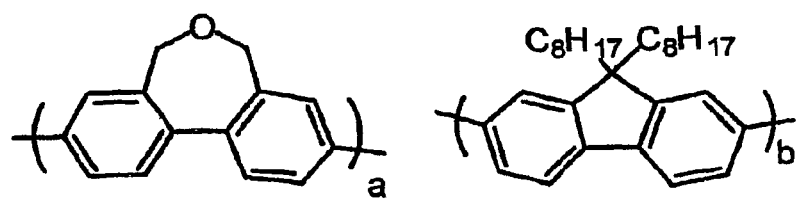
Figure 9:
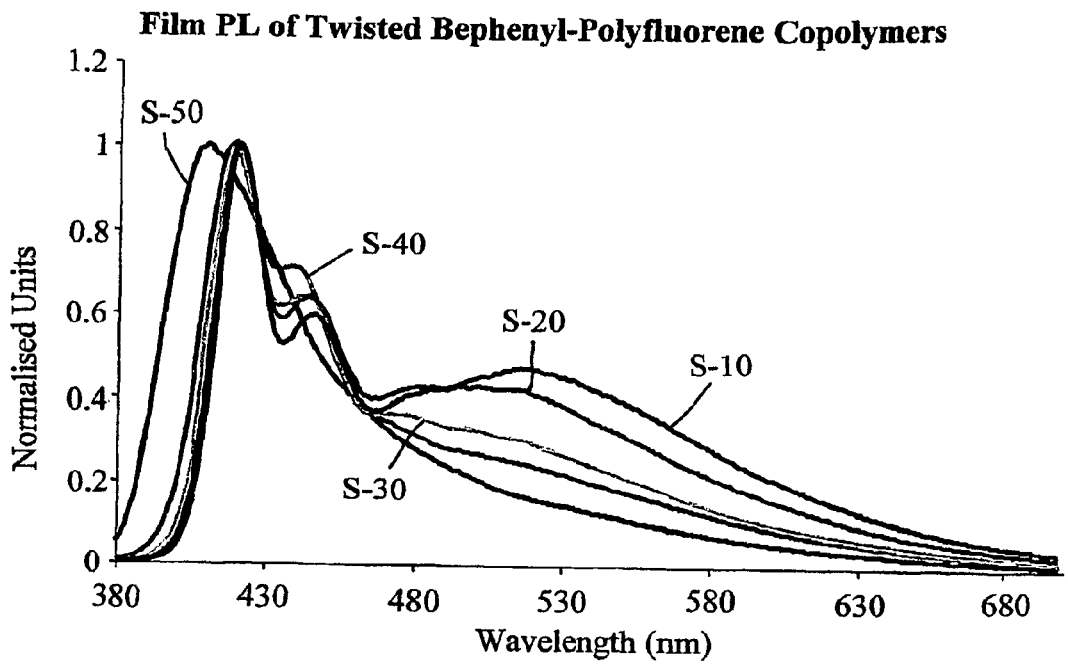
FIG. 9 Thin film photoluminescence spectra for the designated copolymers (excitation wavelength 360 nm).
Figure 9:
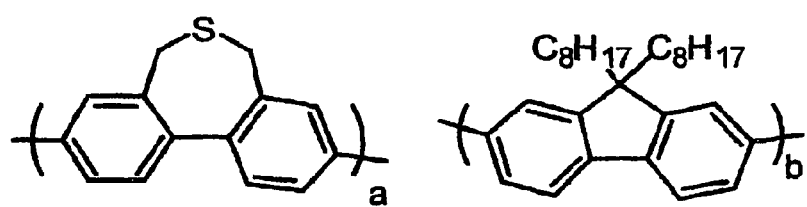
Figure 10:
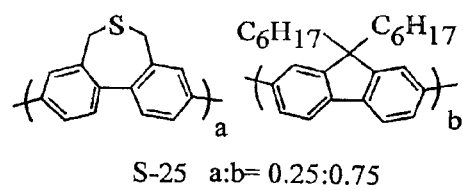
FIG. 10 Electroluminescence spectrum for the PF6 copolymer 36 (m=75; n=25) shown in the attached figure. Device construction was according to the procedure outlined in this document.
Figure 10:
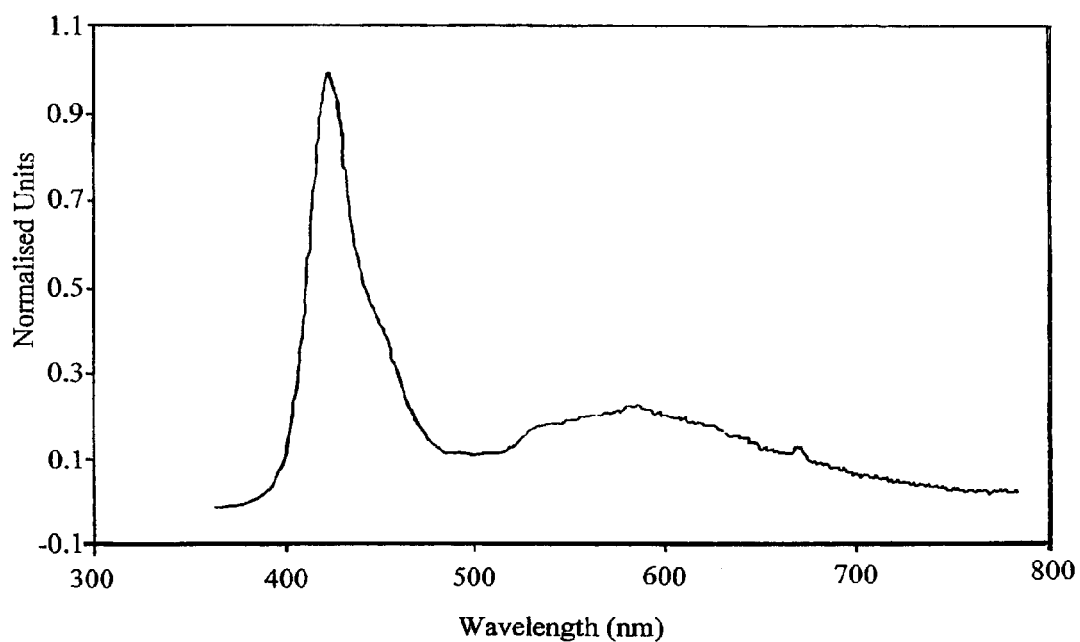

An indium-tin oxide (ITO) coated glass substrate was patterned in stripes (3 mm in width) and washed with water, acetone and ethanol. A hole-injection layer, Poly(3,4-ethylene-dioxythiophene):poly(styrene sulfonic acid) (PEDT-PSS), was spin-coated (2000 rpm, 30 seconds) onto the ITO. The PEDT:PSS layer was dried on a hotplate (130° C.) for 5 minutes. Next, the light-emitting polymer F prepared in Example 3 above was spin-coated on top of the PEDT:PSS layer. Then, the device was transferred to a high-vacuum coating unit and set with a shadow mask (2 mm stripes). A cathode metal, calcium, was deposited on the organic layers through the shadow mask, followed by deposition of aluminium. The size of each pixel is 3 mm×2 mm. The device was finally encapsulated to keep out moisture. The deposition was carried out under high vacuum (1×10$^{-5}$ mbar). Generally, PEDT:PSS is provided as aqueous solution, and light-emitting polymers are prepared as solutions in organic solvent. Low workfunction metals are normally used as a cathode. The typical thicknesses of the layers are as follows. ITO (190 nm)/PEDT:PSS (50 nm)/light-emitting polymer (60 nm)/Ca (40 nm)/Al (200 nm). The devices were examined by applying d.c. bias (0 to 30 V) to the electrodes. The electroluminescent characteristics were measured with a Hewlett-Packard E3631A DC Power Supply, Keithley 2000 Digital Multimeter, Topcon BM-8 Luminance Meter, and Aminco-Bowman. A schematic diagram depicting the structure of the device is shown in FIG. 7 (PF in this diagram refers to the copolymer F of Example 3). A further device, which was prepared almost identically to above, but in which the Ca layer was excluded, was also prepared.

Various physical characteristics of the devices thus prepared were measured and are set out below in Table 2.

TABLE 2

| | | | | Data for polymer 36 | | | | | |
|---|---|---|---|---|---|---|---|---|---|
| Name | HTL pedt-nm | thick (nm) | Max lum (Cd/m$^2$) | @ V (V) | @ J (mA/cm$^2$) | Max iqe. (%) | Max lm/W | Max Cd/A | Von (V) (10 mCd/m$^2$) |
| fcm01. | Ca—Al | 50 | 60 | 20.24 | 7 | 168.8 | 0.04196 | 0.005373 | 0.01199 | 3.8–5 |
| fcm02. | Al | 50 | 60 | 0.5253 | 8.5 | 646.7 | 0.00044 | 3e−05 | 8.12e−05 | 6.4 |

Figure 6:
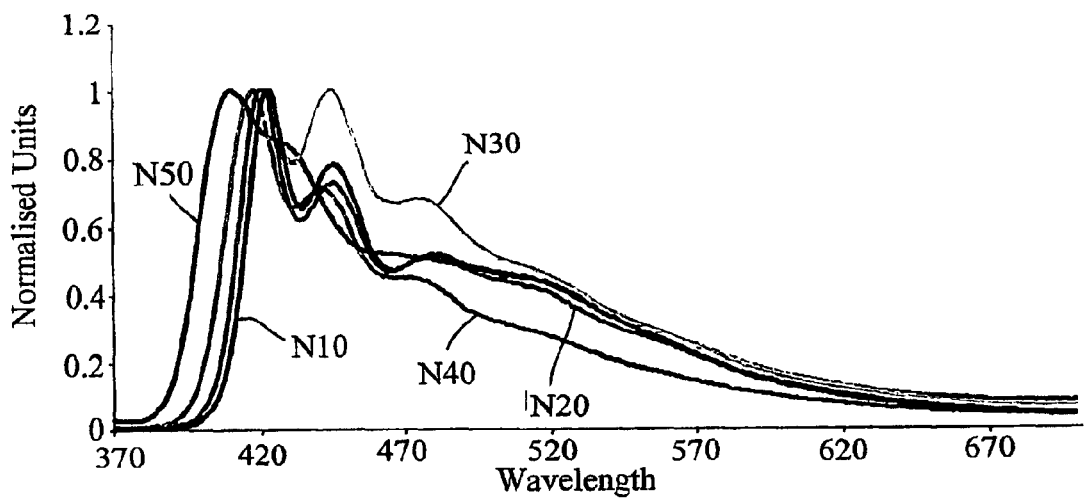
FIG. 6 Thin film photoluminescence spectra for the designated copolymers (excitation wavelength 360 nm)
Figure 6:
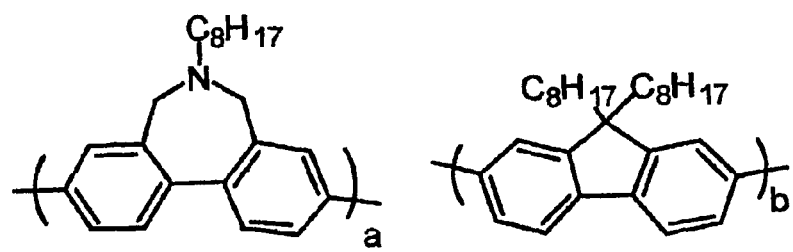

HTL = hole transport layer
thick = thickness of LEP layer
max lum = maximum luminescence efficiency
@V = voltage to achieve maximum luminescence
@J = current density
max iqe = maximum internal quantum efficiency A current voltage luminescence curve for the fcm01 device above is shown in FIG. 6.

What is claimed is:

1. An electroluminescent device comprising a substrate, a first electrode supported by the substrate, a second electrode positioned over the first electrode, and a layer including at least one semiconductive polymer between the first and second electrodes, wherein said semiconductive polymer is a copolymer in which one of the repeat units is a group of formula (I) or a homopolymer in which the repeat unit is a group of formula (I):

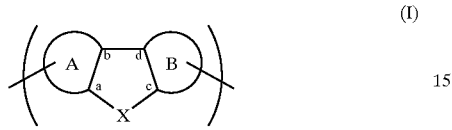

(I)

wherein:
A and B are the same or different and each comprises wholly or partially an aryl moiety or a heteroaryl moiety, said moiety in A being fused to the bond a-b and said moiety in B being fused to the bond c-d; and
X is a linking unit, X being such that there is a torsion angle of at least 5° between the bond a-b and the bond c-d about the bond b-d.

2. An electroluminescent device according to claim 1, wherein said aryl moiety is an aromatic hydrocarbon moeity having from six to 14 carbon atoms in one or more rings which may optionally be substituted with at least one substituent selected from the group consisting of nitro groups, cyano groups, amino groups, alkyl groups, haloalkyl groups, alkoxyalkyl groups, aryloxy groups and alkoxy groups;
wherein the alkyl groups are straight or branched-chain alkyl groups having from one to 20 carbon atoms;
the haloalkyl groups are alkyl groups which are substituted with at least one halogen atom;
the alkoxy groups are straight or branched-chain alkoxy groups having from one to 20 carbon atoms;
the alkoxyalkyl groups are alkyl groups which are substituted with at least one alkoxy group; and
the aryl moiety of the aryloxy groups is an aromatic hydrocarbon group having from six to 14 carbon atoms in one or more rings which may optionally be substituted with at least one substituent selected from the group consisting of nitro groups, cyano groups, amino groups, alkyl groups, haloalkyl groups, alkoxyalkyl groups and alkoxy groups.

3. An electroluminescent device according to claim 1, wherein said heteroaryl moiety is a 5- to 7-membered aromatic heterocyclic moiety containing from one to three heteroatoms selected from the group consisting of sulfur atoms, oxygen atoms and nitrogen atoms, said moiety optionally being substituted with at least one substituent selected from the group consisting of nitro groups, cyano groups, amino groups, alkyl groups, haloalkyl groups, alkoxyalkyl groups, aryloxy groups and alkoxy groups;
wherein the alkyl groups are straight or branched-chain alkyl groups having from one to 20 carbon atoms;
the haloalkyl groups are alkyl groups which are substituted with at least one halogen atom;
the alkoxy groups are straight or branched-chain alkoxy groups having from one to 20 carbon atoms;
the alkoxyalkyl groups are alkyl groups which are substituted with at least one alkoxy group; and
the aryl moiety of the aryloxy groups is an aromatic hydrocarbon group having from six to 14 carbon atoms in one or more rings which may optionally be substituted with at least one substituent selected from the group consisting of nitro groups, cyano groups, amino groups, alkyl groups, haloalkyl groups, alkoxyalkyl groups and alkoxy groups.

4. An electroluminescent device according to claim 1, wherein said repeat unit of formula (I) is a group of formula (II):

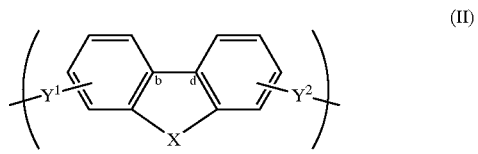

(II)

wherein:
$Y^1$ and $Y^2$ are the same or different and each represents a single bond or a linking unit that is conjugated with the phenyl group to which it is attached; and
X is a linking unit, X being such that there is a torsion angle of at least 5° between the two phenyl groups about the bond b-d.

5. An electroluminescent device according to claim 4, wherein each of $Y^1$ and $Y^2$ is a single bond.

6. An electroluminescent device according to claim 1, wherein said repeat unit of formula (I) is a group of formula (III):

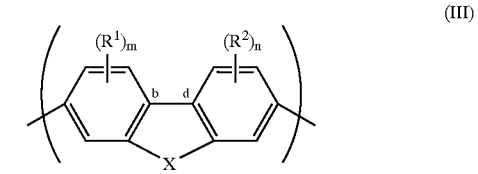

(III)

wherein:
m and n are the same or different and each is 0 or an integer of 1, 2 or 3;
$R^1$ and $R^2$ are same or different and each is selected from the group consisting of alkyl groups, haloalkyl groups, alkoxy groups, alkoxyalkyl groups, aryl groups, aryloxy groups, and aralkyl groups;
wherein the alkyl groups are straight or branched-chain alkyl groups having from one to 20 carbon atoms;
the haloalkyl groups are alkyl groups which are substituted with at least one halogen atom;
the alkoxy groups are straight or branched-chain alkoxy groups having from one to 20 carbon atoms;
the alkoxyalkyl groups are alkyl groups which are substituted with at least one alkoxy group;
the aryl groups are aromatic hydrocarbon groups having from six to 14 carbon atoms in one or more rings which may optionally be substituted with at least one substituent selected from the group consisting of nitro groups, cyano groups, amino groups, alkyl groups, haloalkyl, alkoxyalkyl groups, alkoxy groups, aryloxy groups, and aralkyl groups;
the aryl moiety of the aryloxy group is an aromatic hydrocarbon group having from six to 14 carbon atoms in one or more rings which may optionally be substituted with at least one substituent selected from the group consisting of nitro groups, cyano groups, amino groups, alkyl groups, haloalkyl groups, alkoxyalkyl groups and alkoxy groups;

the aralkyl groups are alkyl groups which are substituted with at least one aryl group; and X is a linking unit, X being such that there is a torsion angle of at least 5° between the two phenyl rings about the bond b-d.

7. An electroluminescent device according to claim 6, wherein X is a moiety of formula -A-B-C- wherein:

A, B and C are the same or different and each is selected from the group consisting of O, S, SO, $SO_2$, $NR^3$, $N^+(R^{3'})(R^{3''})$, $C(R^4)(R^5)$, $Si(R^{4'})(R^{5'})$, and $P(O)(OR^6)$;

$R^3$, $R^{3'}$ and $R^{3''}$ are the same or different and each is selected from the group consisting of hydrogen atoms, alkyl groups, haloalkyl groups, alkoxy groups, alkoxyalkyl groups, aryl groups, aryloxy groups, aralkyl groups, and alkyl groups which are substituted with at least one group of formula —$N^+(R^7)_3$ wherein each group $R^7$ is the same or different and is selected from the group consisting of hydrogen atoms, alkyl groups and aryl groups;

$R^4$, $R^5$, $R^{4'}$ and $R^{5'}$ are the same or different and each is selected from the group consisting of hydrogen atoms, alkyl groups, haloalkyl groups, alkoxy groups, halogen atoms, nitro groups, cyano groups, alkoxyalkyl groups, aryl groups, aryloxy groups, aralkyl groups and alkyl groups which are substituted with a substituent selected from the group consisting of aryl groups, heteroaryl groups, fluorenyl groups and spirobifluorenyl groups, said aryl, heteroaryl, fluorenyl and spirobifluorenyl groups being substituted with a disubstituted amino group the substituents of which are the same or different and are selected from the group consisting of aryl groups, heteroaryl groups, fluorenyl groups and spirobifluorenyl groups, or $R^4$ and $R^5$ together with the carbon atom to which they are attached represent a carbonyl group;

$R^6$ is selected from the group consisting of hydrogen atoms, alkyl groups, haloalkyl groups, alkoxyalkyl groups, aryl groups, aryloxy groups and aralkyl groups; and said heteroaryl groups are 5- to 7-membered aromatic heterocyclic groups containing from one to three heteroatoms selected from the group consisting of sulfur atoms, oxygen atoms and nitrogen atoms, said groups optionally being substituted with at least one substituent selected from the group consisting of nitro groups, cyano groups, amino groups, alkyl groups, haloalkyl groups, alkoxyalkyl groups, aryloxy groups and alkoxy groups.

8. An electroluminescent device according to claim 7, wherein m and n are each 0 and X is a linking unit of formula -A-B-C- wherein A and C each represent a methylene group and B is selected from the group consisting of O, S, $SO_2$, $NR^3$, $N^+(R^{3'})(R^{3''})$ and $C(R^4)(R^5)$.

9. An electroluminescent device according to claim 7, wherein m and n are each 0 and X is a linking unit of formula -A-B-C- wherein A and C each represent O or S and B is a group of formula $C(R^4)(R^5)$ wherein $R^4$ and $R^5$ are the same or different and each represents a hydrogen atom or an alkyl group having from one to ten carbon atoms.

10. An electroluminescent device according to claim 7, wherein the unit of formula (III) is selected from the following group:

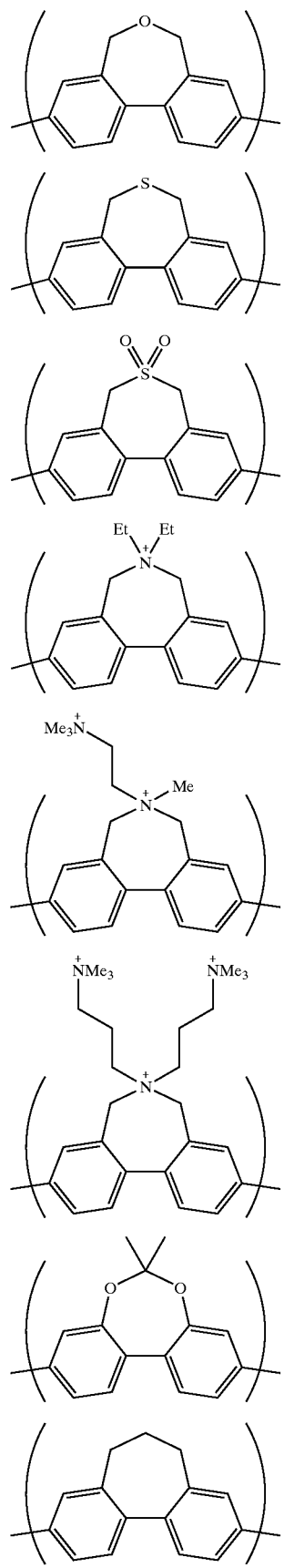

-continued

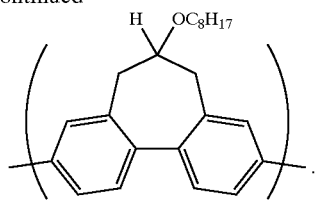

11. A semiconductive polymer, wherein said semiconductive polymer is a copolymer in which one of the repeat units is a group of formula (II) or a homopolymer in which the repeat unit is a group of formula (II):

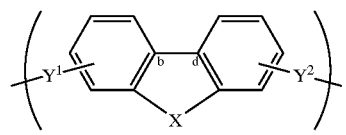

wherein:

$Y^1$ and $Y^2$ are the same or different and each represents a single bond or a linking unit that is conjugated with the phenyl group to which it is attached; and X is a linking unit, X being such that there is a torsion angle of at least 5° between the two phenyl groups about the bond b-d;

with the proviso that, where $Y^1$ and $Y^2$ each represent a single bond, X may not represent a linking unit selected from the group consisting of —CO—O—CO—, —CO—NH—CO— and —O—P(O)(OH)—O—, and where $Y^1$ represents a phenyl group which is fused with the phenyl group to which it is attached to form a naphthalenyl group and $Y^2$ represents a phenyl group which is fused with the phenyl group to which it is attached to form a naphthalenyl group, X may not represent a group of formula —O—CH$_2$—O—.

12. A semiconductive polymer, wherein said semiconductive polymer is a copolymer in which one of the repeat units is a group of formula (III) or a semiconductive homopolymer in which the repeat unit is a group of formula (III):

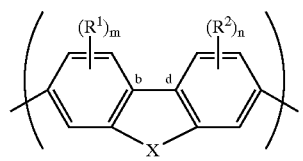

wherein:

m and n are the same or different and each is 0 or an integer of 1, 2 or 3;

$R^1$ and $R^2$ are same or different and each is selected from the group consisting of alkyl groups, haloalkyl groups, alkoxy groups, alkoxyalkyl groups, aryl groups, aryloxy groups, and aralkyl groups;

wherein the alkyl groups are straight or branched-chain alkyl groups having from one to 20 carbon atoms;

the haloalkyl groups are alkyl groups which are substituted with at least one halogen atom;

the alkoxy groups are straight or branched-chain alkoxy groups having from one to 20 carbon atoms;

the alkoxyalkyl groups are alkyl groups which are substituted with at least one alkoxy group;

the aryl groups are aromatic hydrocarbon groups having from six to 14 carbon atoms in one or more rings which may optionally be substituted with at least one substituent selected from the group consisting of nitro groups, cyano groups, amino groups, alkyl groups, haloalkyl, alkoxyalkyl groups, alkoxy groups, aryloxy groups, and aralkyl groups;

the aryl moiety of the aryloxy group is an aromatic hydrocarbon group having from six to 14 carbon atoms in one or more rings which may optionally be substituted with at least one substituent selected from the group consisting of nitro groups, cyano groups, amino groups, alkyl groups, haloalkyl groups, alkoxyalkyl groups and alkoxy groups;

the aralkyl groups are alkyl groups which are substituted with at least one aryl group; and X is a linking unit, X being such that there is a torsion angle of at least 5° between the two phenyl rings about the bond b-d;

with the proviso that, where $R^1$ and $R^2$ are bound by a single bond, X may not represent a linking unit selected from the group consisting of —CO—O—CO—, —CO—NH—CO— and —O—P(O)(OH)—O—.

13. A semiconductive polymer according to claim 12, wherein the polymer is selected from copolymers of the following general formulae (IV), (V), (VI) and (VII):

 (IV)

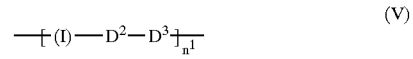 (V)

 (VI)

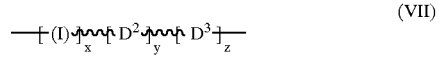 (VII)

wherein:

(I) is a repeat unit of formula III; and $D^1$, $D^2$ and $D^3$ are repeat units which are conjugated with the adjacent units in the polymer chain, $n^1$ is an integer greater than 3, the ratio of x:y is from 99:1 to 1:99, and the ratio of x:(y+z) is from 99:1 to 1:99.

14. A semiconductive polymer according to claim 13, wherein the repeat units $D^1$, $D^2$ and $D^3$ are selected from the following conjugated units of formulae (VIII), (IX), (X), (XI), (XII), (XIII), (XIV) and (XV):

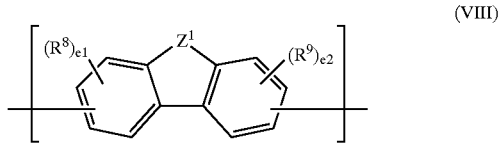 (VIII)

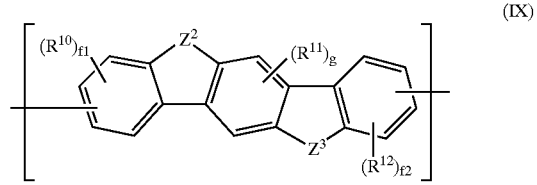 (IX)

-continued

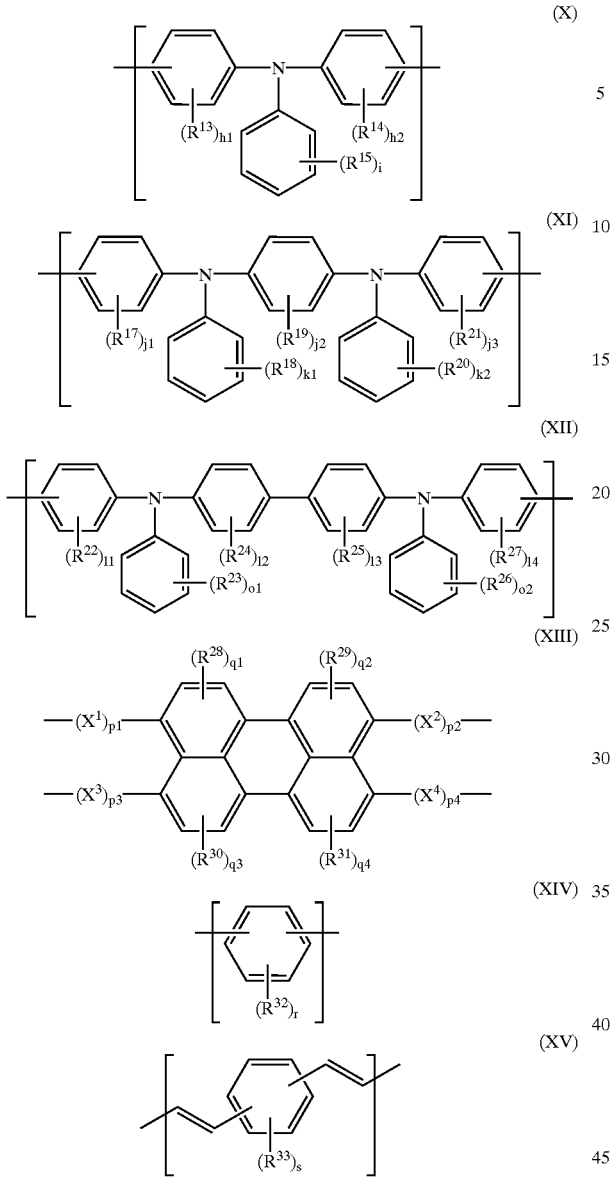

wherein:

each of $R^8$ to $R^{15}$ and $R^{17}$ to $R^{33}$ is the same or different and is selected from the group consisting of alkyl groups, haloalkyl groups, alkoxy groups, alkoxyalkyl groups, aryl groups, aryloxy groups, aralkyl groups and groups of formula —$COR^{16}$ wherein $R^{16}$ is selected from the group consisting of hydroxy groups, alkyl groups, haloalkyl groups, alkoxy groups, alkoxyalkyl groups, aryl groups, aryloxy groups, aralkyl groups, amino groups, alkylamino groups including the alkyl groups, dialkylamino groups including two alkyl groups wherein each alkyl group is the same or different, aralkyloxy groups including the aralkyl group and haloalkoxy groups comprising an alkoxy group which is substituted with at least one halogen atom;

each of $Z^1$, $Z^2$ and $Z^3$ is the same or different and is selected from the group consisting of O, S, SO, $SO_2$, $NR^3$, $N^+(R^{3'})(R^{3''})$, $C(R^4)(R^5)$, $Si(R^{4'})(R^{5'})$ and $P(O)(OR^6)$, wherein;

$R^3$, $R^{3'}$ and $R^{3''}$ are the same or different and each is selected from the group consisting of hydrogen atoms, alkyl groups, haloalkyl groups, alkoxy groups, alkoxyalkyl groups, aryl groups, aryloxy groups, aralkyl groups, and alkyl groups which are substituted with at least one group of formula —$N^+(R^7)_3$ wherein each group $R^7$ is the same or different and is selected from the group consisting of hydrogen atoms, alkyl groups and aryl groups;

$R^4$, $R^5$, $R^{4'}$ and $R^{5'}$ are the same or different and each is selected from the group consisting of hydrogen atoms, alkyl groups, haloalkyl groups, alkoxy groups, halogen atoms, nitro groups, cyano groups, alkoxyalkyl groups, aryl groups, aryloxy groups, aralkyl groups and alkyl groups which are substituted with a substituent selected from the group consisting of aryl groups, heteroaryl groups, fluorenyl groups and spirobifluorenyl groups, said aryl, heteroaryl, fluorenyl and spirobifluorenyl groups being substituted with a disubstituted amino group the substituents of which are the same or different and are selected from the group consisting of aryl groups, heteroaryl groups, fluorenyl groups and spirobifluorenyl groups, or $R^4$ and $R^5$ together with the carbon atom to which they are attached represent a carbonyl group; and $R^6$ is selected from the group consisting of hydrogen atoms, alkyl groups, haloalkyl groups, alkoxyalkyl groups, aryl groups, aryloxy groups and aralkyl groups;

said heteroaryl groups are 5- to 7-membered aromatic heterocyclic groups containing from one to three heteroatoms selected from the group consisting of sulfur atoms, oxygen atoms and nitrogen atoms, said groups optionally being substituted with at least one substituent selected from the group consisting of nitro groups, cyano groups, amino groups, alkyl groups, haloalkyl groups, alkoxyalkyl groups, aryloxy groups and alkoxy groups;

each of $X^1$, $X^2$, $X^3$ and $X^4$ is the same or different and is selected from:

aryl moieties having from six to 14 carbon atoms in one or more rings which may optionally be substituted with at least one substituent selected from the group consisting of nitro groups, cyano groups, amino groups, alkyl groups, haloalkyl groups, alkoxyalkyl groups, aryloxy groups and alkoxy groups;

straight or branched-chain alkylene groups having from one to six carbon atoms;

straight or branched-chain alkenylene groups having from two to six carbon atoms; and straight or branched-chain alkynylene groups having from one to six carbon atoms; or $X^1$ and $X^2$ together and/or $X^3$ and $X^4$ together can represent a linking group of formula (V) below:

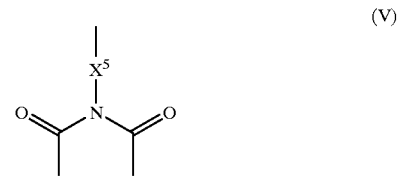

(V)

wherein $X^5$ represents an aryl moiety;

each of e1, e2, f1 and f2 is the same or different and is 0 or an integer of 1 to 3;

each of g, q1, q2, q3 and q4 is the same or different and is 0, 1, or 2;

each of h1, h2, j1, j2, j3, l1, l2, l3, l4, r and s is the same or different and is 0 or an integer of 1 to 4;

each of i, k1, k2, o1 and o2 is the same or different and is 0 or an integer of 1 to 5; and each of p1, p2, p3 and p4 is 0 or 1.

15. A semiconductive polymer according to claim 14, wherein the repeat unit $D^1$, $D^2$ or $D^3$ is a unit of formula (VIII); and $Z^1$, $Z^2$ and $Z^3$ are selected from the group consisting of O, S and $C(R^4)(R^5)$.

16. A semiconductive polymer according to claim 14, wherein said polymer is a statistical copolymer of formula (VI) wherein $D^1$ is selected from the conjugated units of formulae (VIII), (IX), (X), (XI), (XII), (XIII), (XIV), and (XV)

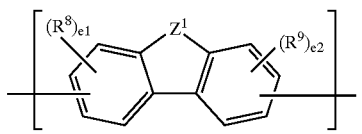

(VIII)

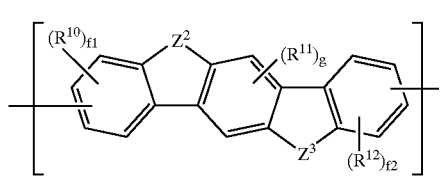

(IX)

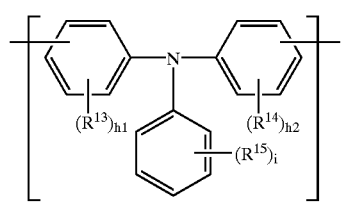

(X)

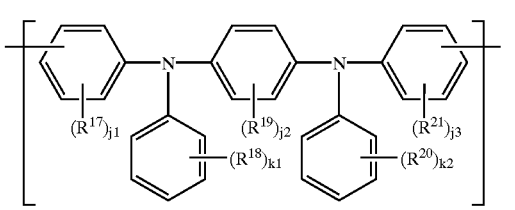

(XI)

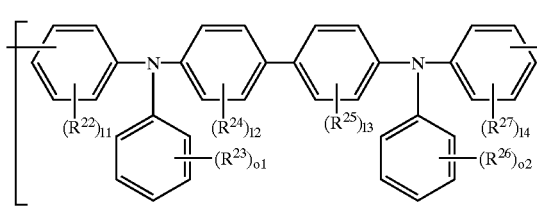

(XII)

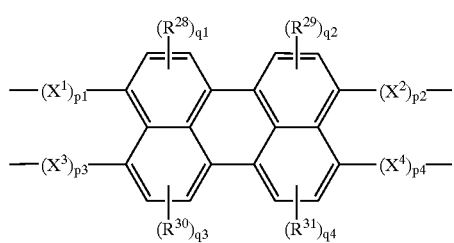

(XIII)

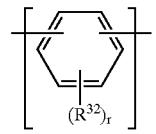

(XIV)

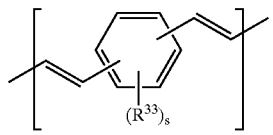

(XV)

and the ratio x:y is from 10:90 to 50:50.

17. An optical device comprising a substrate and at least one semiconductive polymer supported by said substrate, wherein said semiconductive polymer is selected from copolymers of the following general formulae (IV), (V), (VI) and (VII):

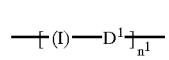

(IV)

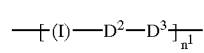

(V)

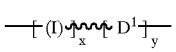

(VI)

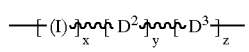

(VII)

wherein:

(I) is a repeat unit of formula III;

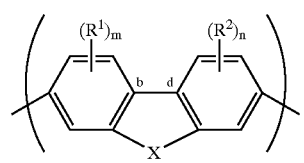

(III)

wherein:

m and n are the same or different and each is 0 or an integer of 1, 2 or 3;

$R^1$ and $R^2$ are same or different and each is selected from the group consisting of alkyl groups, haloalkyl groups, alkoxy groups, alkoxyalkyl groups, aryl groups, aryloxy groups, and aralkyl groups;

wherein the alkyl groups are straight or branched-chain alkyl groups having from one to 20 carbon atoms;

the haloalkyl groups are alkyl groups which are substituted with at least one halogen atom;

the alkoxy groups are straight or branched-chain alkoxy groups having from one to 20 carbon atoms;

the alkoxyalkyl groups are alkyl groups which are substituted with at least one alkoxy group;

the aryl groups are aromatic hydrocarbon groups having from six to 14 carbon atoms in one or more rings which may optionally be substituted with at least one substituent selected from the group consisting of nitro groups, cyano groups, amino groups, alkyl groups, haloalkyl, alkoxyalkyl groups, alkoxy groups, aryloxy groups, and aralkyl groups;

the aryl moiety of the aryloxy group is an aromatic hydrocarbon group having from six to 14 carbon atoms in one or more rings which may optionally be substituted with at least one substituent selected from the group consisting of nitro groups, cyano groups, amino groups, alkyl groups, haloalkyl groups, alkoxyalkyl groups and alkoxy groups;

the aralkyl groups are alkyl groups which are substituted with at least one aryl group;

X is a linking unit, X being such that there is a torsion angle of at least 5° between the two phenyl rings about the bond b-d;

with the proviso that, where $R^1$ and $R^2$ are bound by a single bond, X may not represent a linking unit selected from the group consisting of —CO—O—CO—, —CO—NH—CO— and —O—P(O)(OH)—O—, and $D^1$, $D^2$ and $D^3$ are repeat units which are conjugated with the adjacent units in the polymer chain, $n^1$ is an integer greater than 3, the ratio of x:y is from 99:1 to 1:99, and the ratio of x:(y+z) is from 99:1 to 1:99.

18. An optical device comprising a substrate and at least one semiconductive polymer supported by said substrate, wherein said semiconductive polymer is a copolymer in which one of the repeat units is a group of formula (II) or a homopolymer in which the repeat unit is a group of formula (II):

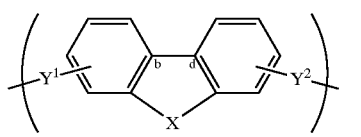

(II)

wherein:
$Y^1$ and $Y^2$ are each single bonds; and
X is a linking unit, X being such that there is a torsion angle of at least 5° between the two phenyl groups about the bond b-d.

19. An optical device comprising a substrate and at least one semiconductive polymer supported by said substrate, wherein said semiconductive polymer is a copolymer in which one of the repeat units is a group of formula (III) or a homopolymer in which the repeat unit is a group of formula (III):

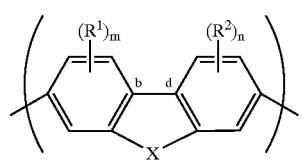

(III)

wherein:
m and n are the same or different and each is 0 or an integer of 1, 2 or 3;
$R^1$ and $R^2$ are same or different and each is selected from the group consisting of alkyl groups, haloalkyl groups, alkoxy groups, alkoxyalkyl groups, aryl groups, aryloxy groups, and aralkyl groups;
wherein the alkyl groups are straight or branched-chain alkyl groups having from one to 20 carbon atoms;
the haloalkyl groups are alkyl groups which are substituted with at least one halogen atom;
the alkoxy groups are straight or branched-chain alkoxy groups having from one to 20 carbon atoms;

the alkoxyalkyl groups are alkyl groups which are substituted with at least one alkoxy group;
the aryl groups are aromatic hydrocarbon groups having from six to 14 carbon atoms in one or more rings which may optionally be substituted with at least one substituent selected from the group consisting of nitro groups, cyano groups, amino groups, alkyl groups, haloalkyl, alkoxyalkyl groups, alkoxy groups, aryloxy groups, and aralkyl groups;
the aryl moiety of the aryloxy group is an aromatic hydrocarbon group having from six to 14 carbon atoms in one or more rings which may optionally be substituted with at least one substituent selected from the group consisting of nitro groups, cyano groups, amino groups, alkyl groups, haloalkyl groups, alkoxyalkyl groups and alkoxy groups;
the aralkyl groups are alkyl groups which are substituted with at least one aryl group; and
X is a linking unit, X being such that there is a torsion angle of at least 5° between the two phenyl rings about the bond b-d.

20. An optical device according to claim 19, wherein X is a moiety of formula -A-B-C- wherein:
A, B and C are the same or different and each is selected from the group consisting of O, S, SO, $SO_2$, $NR^3$, $N^+(R^{3'})(R^{3''})$, $C(R^4)(R^5)$, $Si(R^{4'})(R^{5'})$, and $P(O)(OR^6)$;
$R^3$, $R^{3'}$ and $R^{3''}$ are the same or different and each is selected from the group consisting of hydrogen atoms, alkyl groups, haloalkyl groups, alkoxy groups, alkoxyalkyl groups, aryl groups, aryloxy groups, aralkyl groups, and alkyl groups which are substituted with at least one group of formula —$N^+(R^7)_3$ wherein each group $R^7$ is the same or different and is selected from the group consisting of hydrogen atoms, alkyl groups and aryl groups;
$R^4$, $R^5$, $R^{4'}$ and $R^{5'}$ are the same or different and each is selected from the group consisting of hydrogen atoms, alkyl groups, haloalkyl groups, alkoxy groups, halogen atoms, nitro groups, cyano groups, alkoxyalkyl groups, aryl groups, aryloxy groups, aralkyl groups and alkyl groups which are substituted with a substituent selected from the group consisting of aryl groups, heteroaryl groups, fluorenyl groups and spirobifluorenyl groups, said aryl, heteroaryl, fluorenyl and spirobifluorenyl groups being substituted with a disubstituted amino group the substituents of which are the same or different and are selected from the group consisting of aryl groups, heteroaryl groups, fluorenyl groups and spirobifluorenyl groups, or $R^4$ and $R^5$ together with the carbon atom to which they are attached represent a carbonyl group;
$R^6$ is selected from the group consisting of hydrogen atoms, alkyl groups, haloalkyl groups, alkoxyalkyl groups, aryl groups, aryloxy groups and aralkyl groups; and
said heteroaryl groups are 5- to 7-membered aromatic heterocyclic groups containing from one to three heteroatoms selected from the group consisting of sulfur atoms, oxygen atoms and nitrogen atoms, said groups optionally being substituted with at least one substituent selected from the group consisting of nitro groups, cyano groups, amino groups, alkyl groups, haloalkyl groups, alkoxyalkyl groups, aryloxy groups and alkoxy groups.

21. An optical device according to claim 20, wherein m and n are each 0 and X is a linking unit of formula -A-B-C- wherein A and C each represent a methylene group and B is selected from the group consisting of O, S, SO$_2$, NR$^3$, N$^+$(R$^3$')(R$^3$") and C(R$^4$)(R$^5$).

22. An optical device according to claim 20, wherein m and n are each 0 and X is a linking unit of formula -A-B-C- wherein A and C each represent O or S and B is a group of formula C(R$^4$)(R$^5$) wherein R$^4$ and R$^5$ are the same or different and each represents a hydrogen atom or an alkyl group having from one to ten carbon atoms.

23. An optical device according to claim 20, wherein the unit of formula (III) is selected from the following group:

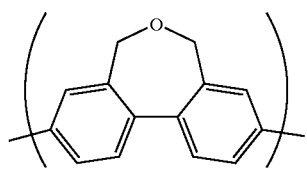

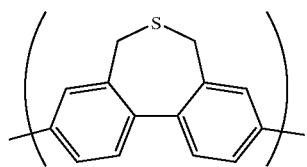

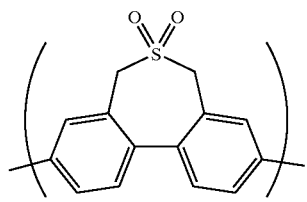

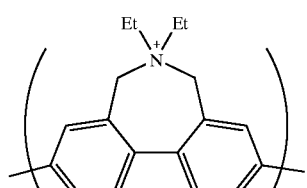

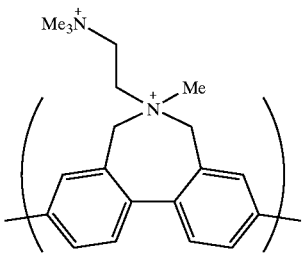

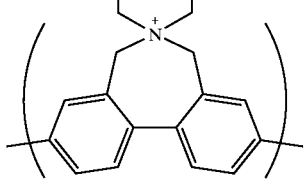

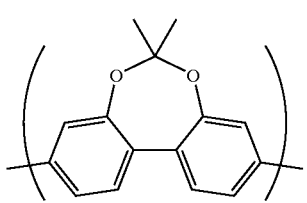

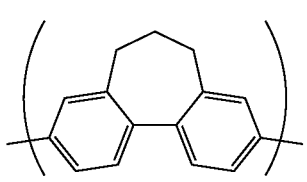

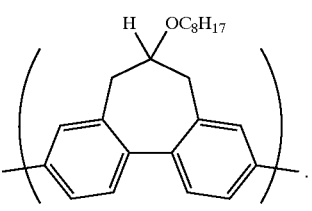

* * * * *